US008170889B2

(12) United States Patent
Pearson et al.

(10) Patent No.: US 8,170,889 B2
(45) Date of Patent: May 1, 2012

(54) METHODS AND SYSTEMS FOR EVALUATING INTERACTION OF MEDICAL PRODUCTS AND DEPENDENCE ON DEMOGRAPHIC VARIABLES

(75) Inventors: Ronald K. Pearson, Harrisburg, PA (US); Alan M. Hochberg, Harrisburg, PA (US)

(73) Assignee: UBC Late Stage, Inc., Kansas City, MO (US)

( * ) Notice: Subject to any disclaimer, the term of this patent is extended or adjusted under 35 U.S.C. 154(b) by 559 days.

(21) Appl. No.: 12/065,631

(22) PCT Filed: Sep. 22, 2006

(86) PCT No.: PCT/US2006/037151
§ 371 (c)(1),
(2), (4) Date: Apr. 6, 2008

(87) PCT Pub. No.: WO2007/038375
PCT Pub. Date: Apr. 5, 2007

(65) Prior Publication Data
US 2008/0215402 A1    Sep. 4, 2008

Related U.S. Application Data

(60) Provisional application No. 60/719,173, filed on Sep. 22, 2005.

(51) Int. Cl.
*G06F 19/00* (2006.01)
(52) U.S. Cl. .......................................................... 705/3
(58) Field of Classification Search .................. 705/2, 3, 705/19; 1/1; 395/613; 435/6
See application file for complete search history.

(56) References Cited

U.S. PATENT DOCUMENTS

| 5,752,025 A * | 5/1998 | Shakib et al. .......................... 1/1 |
| 6,493,637 B1 | 12/2002 | Steeg |
| 6,703,202 B2 * | 3/2004 | McGrath et al. .................. 435/6 |

OTHER PUBLICATIONS

David M. Coulter et al., "Antipsychotic drugs and heart muscle disorder in international pharmacovigilance: data mining study", BMJ vol. 322, May 19, 2001, pp. 1207-1209.
John R. Vokey et al., "Multiway Frequency Analysis for Experimental Psychologists", Canadian Journal of Experimental Psychology, 2003, 57:3, 257-264.

(Continued)

*Primary Examiner* — Gerald J. O'Connor
*Assistant Examiner* — John Pauls
(74) *Attorney, Agent, or Firm* — Woodcock Washburn LLP

(57) ABSTRACT

A computer implemented method of evaluating interaction two or more medical products or conditions, in the context of a reference condition, based on a dataset of patient records includes developing a reference contingency lattice of lattice subsets from a subset of the patient records containing the reference condition, wherein the lattice subsets correspond to the number of patient records that contain each of the two or more medical products or conditions and combinations thereof. A plurality of comparison contingency lattices are developed, each of the comparison contingency lattices developed from a respective random subset of patient records not containing the reference condition, where each of the comparison contingency lattices include lattice subsets that correspond to the number of patient records that contain each of the two or more medical products or conditions and combinations thereof. The lattice subsets of the reference contingency lattice are compared to the corresponding lattice subsets of the comparison contingency lattices to determine whether a lattice subset is indicative of an interaction between the medical products or conditions with respect to the reference condition.

29 Claims, 10 Drawing Sheets

OTHER PUBLICATIONS

Gerd Stumme et al., "Computing iceberg concept lattices with Titanic", Data & Knowledge Engineering 42 (2002) 189-222.

B.A. Davey et al., Introduction to Lattices and Order, Cambridge University Press, 1990, pp. 1-26.

Roderick J.A. Little et al., "Statistical Analysis with Missing Data", Wiley-Interscience, 2002, pp. 60-74.

Alan Agresti et al., "Categorical Data Analysis", Second Edition, Wiley-Interscience, 2002, pp. 43-47.

Peter H. Westfall et al., "Resampling-Based Multiple Testing—Examples and Methods for p-Value Adjustment", John Wiley & Sons Inc., pp. 43-46. Copyright 1993.

Uta Priss, "Formal Concept Analysis in Information Science", Annual Review of Information Science & Technology, Vol. 40, 2006, pp. 521-543.

Ronald K. Pearson, "Mining Imperfect Data", Society for Industrial and Applied Mathematics, Philadelphia Pa, 2005, pp. 159-161.

* cited by examiner

METHODS AND SYSTEMS FOR EVALUATING INTERACTION OF MEDICAL PRODUCTS AND DEPENDENCE ON DEMOGRAPHIC VARIABLES

RELATED APPLICATIONS

This application claims the benefit of priority to U.S. provisional application No. 60/719,173, filed on Sep. 22, 2005.

BACKGROUND

Analysis of pharmacovigilance data for drug interactions or other causes of adverse events has been an important endeavor in order to maximize the safety of patients, and discovery of such interactions and other causes of adverse events as quickly and efficiently as possible is of utmost importance. While statistical methods to analyze pharmacovigilance data have been used extensively, many suffer from several deficiencies. For example, many of the statistical techniques used do not adequately account for the "bystander effect" in which interactions that appear to be caused by the presence of one drug or cause is really the result of the simultaneous presence of another drug or cause.

Furthermore, the known techniques of analysis of pharmacovigilance data also often suffer from the problem that the drug or other interactions (or information) that are present in the data (stored, for example, in a table in a database) are not intuitively or conveniently visualized in a display.

SUMMARY OF THE INVENTION

In certain embodiments, the present invention provides a computer implemented method of evaluating interaction of two or more medical products or conditions, in the context of a reference condition, based on a dataset of patient records. The method includes: developing a reference contingency lattice of lattice subsets from a subset of the patient records containing the reference condition, wherein the lattice subsets correspond to the number of patient records that contain each of the two or more medical products or conditions and combinations thereof; developing a plurality of comparison contingency lattices, each of the comparison contingency lattices developed from a respective random subset of patient records not containing the reference condition, wherein each of the respective random subsets is of the same size as the subset of patient records containing the references condition, and wherein each of the comparison contingency lattices include lattice subsets that correspond to the number of patient records that contain each of the two or more medical products or conditions and combinations thereof; and comparing the lattice subsets of the reference contingency lattice to the corresponding lattice subsets of the comparison contingency lattices to determine whether a lattice subset is indicative of an interaction between the medical products or conditions with respect to the reference condition.

In certain embodiments, the present invention provides a computer-implemented method of evaluating interaction two or more medical products or conditions, in the context of a reference condition, based on a dataset of patient records. The method includes: developing a reference orthogonal contingency lattice of lattice subsets from a subset of the patient records containing the reference condition, wherein the lattice subsets correspond to the number of patient records that contain each of the two or more medical products or conditions and combinations thereof but that exclude all the other medical products or conditions and combinations thereof, respectively; developing a plurality of comparison contingency lattices, each of the comparison contingency lattices developed from a respective random subset of patient records not containing the reference condition, wherein each of the respective random subsets is of the same size as the subset of patient records containing the references condition, and wherein each of the comparison contingency lattices includes lattice subsets that correspond to the number of patient records that contain each of the two or more medical products or conditions and combinations thereof but that exclude all the other medical products or combinations thereof, respectively; and comparing the lattice subsets of the reference contingency lattice to the corresponding lattice subsets of the comparison contingency lattices to determine whether a lattice subset is indicative of an interaction between the medical products or conditions with reference to the reference condition.

In certain embodiments, the present invention provides a computer-implemented method of evaluating interaction of two or more medical products, in the context of a reference condition, based on a dataset of patient records. The method includes: determining a number, N, of patient records in the dataset containing indications of medical product A and medical product B; of patient records in the dataset containing indications of medical product A and medical product B, determining a number, Nx, of patient records containing indications of the reference condition; among patient records, of a first random sample of size N of patient records of the dataset, the patient records of the first random sample containing medical product A and not medical product B, comparing a number of such patient records containing the reference condition to Nx; among patient records of a second random sample of size N of patient records of the dataset, the patient records of the second random sample containing medical product B and not medical product A, comparing a number of such patient records containing the reference condition to Nx; among patient records of a third random sample of size N of patient records of the dataset, the patient records of the third random sample containing neither medical product A or medical product B, comparing a number of such patient records containing the reference condition to Nx; and determining whether a second-order bystander effect exists between the reference condition and either of medical product A and medical product B.

In certain embodiments, the present invention provides a computer-implemented method of evaluating dependence on demographic variables, in the context of a medical product and a reference condition, based on a dataset of patient records. The method includes: determining a number, N, of patient records in the dataset containing indications of both the medical product and the reference condition; for a continuous demographic variable, determine an average of the demographic variable of patient records in a first random sample of size N, the patient records of the first random sample containing an indication of the medical product and not containing an indication of the reference condition; for the continuous demographic variable, determine an average of the demographic variable of patient records in a second random sample of size N, the patient records of the second random sample containing an indication of the reference condition and not containing an indication of the medical product; for the continuous demographic variable, determine an average of the demographic variable of patient records in a third random sample of size N, the patient records of the third random sample containing neither an indication of the medical product or an indication of the reference condition; for a categorical demographic variable, among patient records in a fourth random sample of size N, determine a fraction of patient records for which the categorical demographic variable has a specified value, the patient records of the fourth random sample containing an indication of the medical product and not containing an indication of the reference condition; for the categorical demographic variable, among patient records in a fifth random sample of size N, determine a fraction of patient records for which the categorical demographic variable has a specified value, the patient records of the fifth random sample containing an indication of the reference condition and not containing an indication of the medical product; for the categorical demographic variable, among patient records in a sixth random sample of size N, determine a fraction of patient records for which the categorical demographic variable has a specified value, the patient records of the sixth random sample containing neither an indication of the medical product or an indication of the reference condition; and determining whether a relationship exists between the continuous demographic variable or categorical demographic variable, the reference condition and the medical product.

In accordance with other of its aspects, the present invention provides a computer readable data storage means containing program code recorded thereon for implementing the method steps described herein.

The present invention further provides a computing system having a system memory containing computer readable data storage means containing program code recorded thereon, for implementing the method steps described here.

DETAILED DESCRIPTION OF THE PREFERRED EMBODIMENTS

1 Introduction

Figure 1:
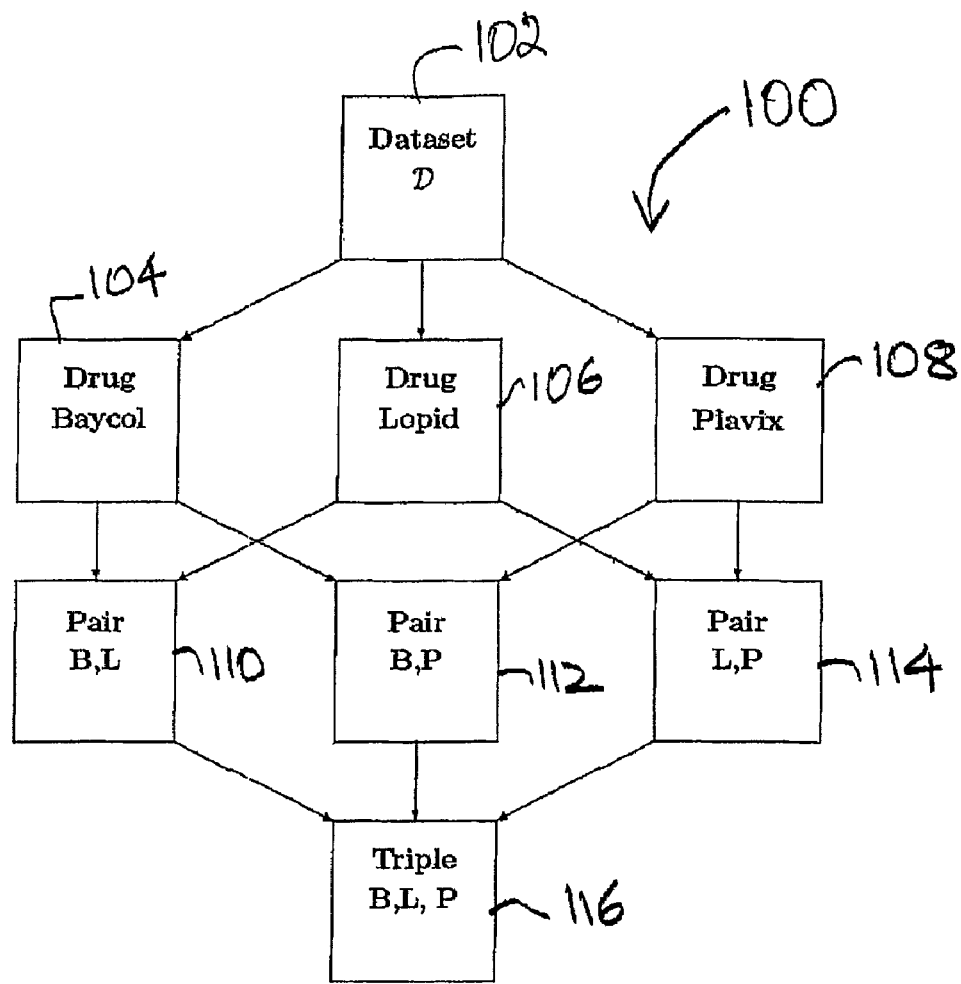
FIG. 1 shows a lattice generated by data from an adverse event reporting database.

In certain embodiments, the present invention provides an approach to assessing multi-way interactions in pharmacovigilance data. This approach uses a lattice-based comparison of datasets, which is also described further herein. In certain embodiments, the following two things are specified:

1. a reference condition, which serves as a basis for generating both a summary of direct interest and a random family of comparison summaries for data records not meeting the reference condition, used to assess the significance of the original result;
2. a set of criteria of primary interest, whose interactions are quantified with respect to the reference condition.

The specific example discussed here takes "rhabdomyolysis" as the reference condition, comparing results obtained from the Adverse Event Reporting System (AERS) database (maintained by the Food and Drug Administration) among patients reporting this reference condition, against random samples of patients not reporting rhabdomyolysis (i.e., the reference condition). The criteria of primary interest in this example are the three drugs Baycol, Lopid, and Plavix, and the objective of the analysis is to assess the evidence in support of associations between rhabdomyolysis and either individual drugs or drug combinations. It should be noted that the particular reference condition described herein as well as the particular drugs (as criteria of primary interest) referenced herein are exemplary only. One skilled in the art would recognize various other alternatives and modification all of which are considered to be a part of the present invention.

The first construction described here is the contingency lattice, which characterizes all possible combinations of the criteria of primary interest, in a way that it displays information that may be stored in a multi-way contingency table. The random permutation-based reference strategy proposed herein basically asks whether the multi-way contingency table generated from the dataset under the reference condition is consistent with those generated from datasets of the same size (or a similar size) that do not satisfy the reference condition. It should be noted that, in certain embodiments, the generated datasets could be a multiple or a fraction of the size of the dataset under the reference condition provided the results are scaled to account for the different sizes of the datasets.

The second construction described is the orthogonalized contingency lattice, an extension of the contingency lattice just described that is designed to reduce bystander effects where the presence of one condition (e.g., the drug Baycol appearing in an adverse event report) induces a spurious association between other conditions (e.g., the presence of the drug Plavix and the occurrence of rhabdomyolysis).

2 Contingency Lattices

A 2×2 contingency table can be used to summarize records that do or do not satisfy two different binary conditions. That is, suppose that Conditions A and B are characterizations of records in a dataset D that can either be satisfied or not satisfied. In pharmacovigilance problems, for example, these conditions would typically be the presence of a specified drug or adverse event in a spontaneous reporting database (or other similar database) like the FDA's AERS database. For example, Condition A might be the presence of the adverse reaction "rhabdomyolysis" in an Individual Safety Report (ISR), and Condition B might be the presence of the drug Baycol (cerivastatin sodium) in the report. Much of what is now done in pharmacovigilance is very closely related to 2×2 contingency tables constructed from such drug-adverse event pairs. These tables are characterized by the following four numbers:

1. $N_{AB}$=the number of reports satisfying both Conditions A and B,
2. $N_A$=the number of reports satisfying Condition A, with or without Condition B, 3. $N._{\cdot B}$=the number of reports satisfying Condition B, with or without Condition A, and
4. $N..$=the total number of reports considered.

In particular, commonly used measures of association between conditions (e.g., the odds ratio) can be computed from these four numbers. See, for example, A. AGRESTI, CATEGORICAL DATA ANALYSIS, $2^{nd}$ ed., Wiley (2002). A key observation is that each of the four numbers listed above represents the size of a well-defined set of records, satisfying the following inclusion conditions:

$$S_{AB} \subset \begin{Bmatrix} S_{A}\cdot \\ S\cdot_{B} \end{Bmatrix} \subset S \ldots \quad (1)$$

These inclusion conditions represent an important example of a partial order. B. A. DAVEY AND H. A. PREISTLEY, INTRODUCTION TO LATTICES AND ORDER, Cambridge University Press, 1990. Therefore, set S precedes set T, written S<T, if S is contained in T as a subset. Note that not all sets are comparable in this partial order: for example, $S_{A}\cdot$ is generally neither contained in nor contains $S._{\cdot B}$. Conversely, note that these two sets exhibit a greatest lower bound (specifically, the set $S_{AB}=S_{A}\cdot \cap S._{\cdot B}$ is the largest set contained in both $S_{A}\cdot$ and $S._{\cdot B}$) and a least upper bound (the set S..).

More generally, a lattice is a special case of a partially ordered set or poset in which it may not be possible to compare all elements of the set directly, but every pair of elements does have both a greatest lower bound (GLB) and a least upper bound (LUB). That is, given two elements x and y and some ordering criterion <, it may not be true that either x<y or y<x, but if x and y are elements of a lattice, it is true that there exist elements a and b such that both a<x and a<y hold, and that x<b and y<b also hold. An important example is the collection of subsets of a set, ordered by inclusion. For concreteness, consider the three-element case, S={x, y, z}. Altogether, there are $2^3=8$ possible subsets:

{x, y, z}, {x, y}, {x, z}, {y, z}, {x], y}, {Z}, ∅ where ∅ denotes the empty set. By definition, the empty set is a subset of all other sets, and it is clear that all one- and two-element sets in this list are subsets of the original set S, but some of these sets are not comparable under the inclusion ordering. For example, since {x, y} neither contains nor is contained in {x, z}, these two sets are not comparable under this order. However, both of these sets contain {x} as a subset and both are contained in the complete set S. These two sets represent the greatest lower bound (i.e., the largest subset common to both) and the least upper bound (i.e., the smallest set containing both), respectively, for the pair of sets {x, y} and {x, z}.

Lattices provide the basis for formal concept analysis (FCA), an area of active research in the data mining community. U. Priss, *Formal Concept Analysis in Information Science*, ANNUAL REVIEW OF INFORMATION SCIENCE, VOL. 40 (to be published). Roughly speaking, FCA is based on lattices defined by mutually-reinforcing sets of data records and attributes. A practical disadvantage of formal concept analysis is that the resulting lattices are often huge. For example, Stumme et al. (cited further herein) note that the total number of formal concepts required to fully characterize the mushroom dataset from the UCI Machine Learning Archive is 32,086 for a dataset containing 23 characterizations of 8,416 mushrooms. G. Stumme, R. Taouil, Y. Bastide, N. Pasquier, and L. Lakhal, *Computing Iceberg Lattices using TITANIC*, DATA AND KNOWLEDGE ENGINEERING, VOL. 42, 189-222 (2002). Examples like this one motivate their development of approximate descriptions in terms of much smaller lattices of concepts with "large support."

Alternatively, any finite collection of binary conditions (i.e., conditions that each individual record either satisfies or does not satisfy) defines a subset lattice, consisting of the subsets satisfying each individual condition and all possible combinations of these conditions. For N conditions, this lattice consists of $2^N$ sets and it corresponds to a multi-way contingency table analogous to the 2×2 contingency table (suitably expanded) discussed above. Typically, multi-way contingency tables involving three or more conditions are analyzed using loglinear models (See A. Agresti at Section 8.4), but the asymmetric nature of these models (i.e., they predict a single response variable from all others, taken as independent stimuli) has been raised as an objection in some applications where it is not natural to separate variables into a single response and N-1 independent stimuli. See J. R. Vokey, *Multiway Frequency Analysis for Experimental Psychologists*, CAN. J. EXPER. PSYCHOLOGY, v. 57, 257-264 (2003). In certain embodiments, the present invention proposes the use of the lattice of these sets as an alternative approach to analyzing these multiway tables.

As a specific example, FIG. 1 shows a lattice 100 generated by the subsets of ISR's from the AERS database listing the following three drugs: B: Baycol (cerivastatin sodium), L: Lopid (gemfibrozil), P: Plavix (clopidogrel bisulfate).

These criteria define three subsets of the patient records in the dataset D, and these subsets in turn generate the subset inclusion lattice 100 shown in FIG. 1. That is, each box (102-116) in this figure represents a subset of patient records from D, with the top box representing all records in the dataset. The three boxes (104, 106, 108) in the second row from the top in this figure correspond to the sets of patient records satisfying each of the three conditions defined above, and the three boxes (110, 112, 114) in the third row correspond to the subsets of patients satisfying each pair of these conditions. Finally, the single box (116) at the bottom corresponds to the subset of patients exhibiting all three of these characteristics. The arrows in this figure point from each set to all of its immediate subsets (i.e., all subsets obtained by imposing one additional condition).

In the basic analysis approach proposed here, given a set of conditions of interest (e.g., the three drugs Baycol, Lopid, and Plavix in the example just described), a corresponding contingency lattice is first constructed, as in FIG. 1. We then characterize all of the sets defined by this lattice in terms of their size, giving a vector of $2^N$ integer-valued components. Finally, we determine whether these numbers are associated with the reference condition by using the random subset-based significance analysis described in the next section. The basic question of interest is whether any of the subsets defining the contingency lattice are larger or smaller than we would expect due to random sampling alone, in the absence of any association between the reference condition that defines dataset D and the conditions of interest defining the lattice of subsets.

3 Randomized References

To interpret contingency lattice results, the contingency lattice as described in the preceding discussion is first constructed, using the records from a dataset $D_R$ that satisfies a specified reference condition R. In the specific example considered in this note, this reference condition is the occurrence of the adverse event "rhabdomyolysis" in each adverse event report (i.e., $D_R$ contains all records for patients reporting rhabdomyolysis). A key assumption is that the reference set $D_R$ is a proper subset of the original dataset D, such that the difference set $D\backslash D_R=D\cap \overline{D}_R$ contains a relatively large number of records compared with $D_R$. Note that this condition is automatically satisfied if $N_R \ll N_D$, as in the example considered here ($N_R=11,773$ vs. $N_D=597,074$). Under this assumption, it is possible to generate a large number M of random subsets of D that do not satisfy the reference condition R. The basic analysis strategy is then to generate M such subsets, construct their associated contingency lattices, and compare the results obtained with the original contingency lattice. If these randomly generated lattices are consistently different from the original contingency lattice, this observation provides evidence of an association between the reference condition R and one or more of the conditions of interest defining the contingency lattice.

The measures of difference considered here are the sizes of the subsets defined by the contingency lattices. It should be recognized that using the sizes as a measure of difference is exemplary only and one skilled in the art would recognize various alternatives and modifications all of which are considered a part of the present invention. Examples of which can include the use of alternative characterizations, such as age or gender. In certain embodiments, each of the randomly generated comparison datasets $\{D_i\}$ is of fixed size $N_R$, and the sizes of the $2^N-1$ other lattice subsets will be denoted $N_{ij}$ where $j=1, 2, \ldots, 2^N-1$ designates the sub-set and $i=1, 2, \ldots, M$ designates the dataset $D_i$ considered. The sizes of the corresponding subsets constructed from the reference dataset $D_R$ are denoted $N_{Rj}$ for $j=1, 2, \ldots, 2^N-1$. Differences between the results obtained for the reference dataset $D_R$ and the random comparison datasets $D_i$ are assessed using the difference between the subset sizes $N_{Rj}$ and $\{N_{ij}\}$ for $i=1, 2, \ldots, M$ for all subsets j. Unusually large values of $N_{Rj}$ relative to $\{N_{ij}\}$ suggest a possible association between the reference condition R and the conditions of interest that define the subset j.

Figure 2:
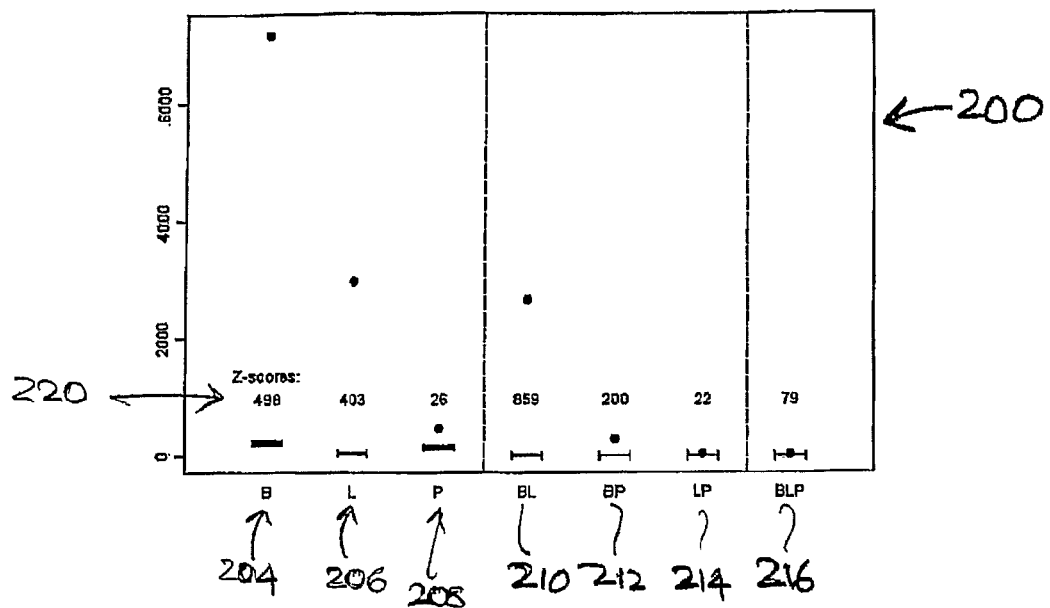
FIG. 2 is an exemplary boxplot that summarizes results from a lattice in which the subset sizes obtained for M=200 comparison sets are compared to the subset sizes for a reference condition from a reference dataset.

Boxplot summaries provide a convenient graphical way of representing these results, highlighting the subsets for which the differences between the primary reference dataset and the randomized comparison datasets are most pronounced. This point is illustrated in FIG. 2, which shows the results 200 obtained for the reference condition "rhabdomyolysis," which defines a reference dataset $D_R$ of size $N_R=11,773$. The solid points shown in FIG. 2 represent the sizes of each of the seven subsets (204-216) of $D_R$ defined by the three conditions of interest (i.e., patient was taking Baycol, Lopid, Plavix, or a combination of these drugs). The boxplots shown in FIG. 2 summarize the subset sizes obtained for M=200 comparison sets $\{D_i\}$, each obtained by randomly selecting $N_R=11,773$ patient records from among those not reporting the reference condition rhabdomyolysis. The fact that some of the reference results (most prominently, those for Baycol (Case B or 204), Lopid (Case L or 206), and Baycol with Lopid (Case BL or 210)) fall well outside the range of the randomized comparison results suggests a significant association between the condition "rhabdomyolysis" and these drugs. FIG. 2 also lists the z-scores 220 associated with each comparison (i.e., between the size of primary reference dataset and the sizes of the randomized comparison subsets). These numbers provide quantitative characterizations of these comparisons and are described in the next section.

4 Interpretation Via Z-Scores

In classical statistics, random variables are frequently assumed to exhibit a Gaussian distribution, which is completely characterized by the population mean $\mu$ and standard deviation $\sigma$. In fact, if $\mu$ and $\sigma$ are known, the probability of observing a sample from this distribution with the value X is completely determined by the value $Z=(X-\mu)/\sigma$. In cases where the Gaussian assumption is reasonable but $\mu$ and $\sigma$ are unknown, these quantities are usually estimated from a sequence of N data samples $\{x_k\}$ as:

$$\hat{\mu} = \frac{1}{N} \sum_{k=1}^{N} x_k, \qquad (2)$$

$$\hat{\sigma} = \sqrt{\frac{1}{N-1} \sum_{k=1}^{N} (x_k - \hat{\mu})^2}.$$

It follows from this result that the probability of observing a specific data value x in an approximately Gaussian data sequence can be reliably estimated from the z-score, the sample analog of Z defined above:

$$z = \frac{x - \hat{\mu}}{\hat{\sigma}}. \qquad (3)$$

For example, z values larger than 3 in absolute value arise with probability less than about 0:3%.

Despite its popularity, the Gaussian assumption often fails to hold; even so, the z-scores can still be used to derive probability bounds that are quite conservative but almost universal. Specifically, so long as the mean and variance of the underlying distribution are finite (a condition that can be violated but generally holds), it follows from Chebyshev's inequality that:

$$P\{|z| > t\} \leq \frac{1}{t^2}. \qquad (4)$$

See R. K. Pearson, *Mining Imperfect Data*, SIAM, Philadelphia, 2005, at page 159. Thus, even for distributions that are extremely non-Gaussian (e.g., highly skewed, heavy-tailed, multi-modal, etc.), large z-scores generally imply rare events.

In the problems considered here, z-scores are computed for the size of each contingency lattice subset constructed under the primary reference condition, relative to the mean $\hat{\mu}$ and standard deviation $\hat{\sigma}$ of the sizes of the corresponding M random comparison subsets. It follows from the above arguments that if the magnitude of the resulting z-score is large, the result obtained under the primary reference condition is not consistent with the randomized comparison results. Such an inconsistency represents evidence that the reference condition significantly influences the size of the corresponding contingency lattice subset. If there is insufficient data regarding a given set of conditions, however, the standard deviation of the numbers in the comparison contingency lattice will increase. This may be taken as an indication that, because of insufficient data, the proposed method has inadequate power to draw conclusions.

As a specific example, the very large z-scores listed in FIG. 2 for Cases B, L, and BL (204, 206, and 210) provide evidence that the drugs Baycol, Lopid and the two together are strongly associated with the adverse event rhabdomyolysis. These results are summarized in Table 1 further herein, which gives the size of each of the seven subsets defined by the three-way contingency lattice for Baycol, Lopid, and Plavix, based on the reference condition rhabdomyolysis. Specifically, this table gives the size of each of the seven subsets for patients reporting rhabdomyolysis, the range of the corresponding subset sizes for M=200 randomly selected samples of patients not reporting rhabdomyolysis, the associated z-scores, and their probability bounds as determined by the Chebyshev inequality (4). The very large z-scores for Baycol and the combination of Baycol and Lopid are consistent with the fact that Baycol was withdrawn from the market because of its associated rhabdomyolysis risk, particularly when taken in combination with Lopid.

TABLE 1

Summary of subset definitions, sizes based on the rhabdomyolysis dataset, minimum and maximum subset sizes from the 200 randomly generated non-rhabdomyolysis datasets, the z-scores characterizing the differences between the rhabdomyolysis and non-rhabdomyolysis datasets, and the corresponding probabilities derived from the Chebyshev inequality. These results correspond to the (non-orthogonalized) contingency lattice; z-scores marked with * are significant at the Bonferroni-corrected 5% significance level ($|z| > 12$).

| Case | $N_{rhabdo}$ | $N_{ref}^-$ | $N_{ref}^+$ | z | $P_{Chebyshev}$ |
|---|---|---|---|---|---|
| B | 7128 | 195 | 265 | 498* | $4.03 \times 10^{-6}$ |
| L | 2982 | 33 | 72 | 403* | $6.16 \times 10^{-6}$ |
| P | 465 | 114 | 177 | 26* | $1.43 \times 10^{-3}$ |
| BL | 2664 | 2 | 21 | 859* | $1.35 \times 10^{-6}$ |
| BP | 290 | 0 | 7 | 200* | $2.50 \times 10^{-5}$ |
| LP | 42 | 0 | 8 | 22* | $2.14 \times 10^{-3}$ |
| BLP | 30 | 0 | 2 | 79* | $1.58 \times 10^{-4}$ |

In deciding whether an individual contingency lattice subset result is significant or not, it is important to account for the fact that we are not making a single comparison, but rather $p=2^N-1$ comparisons. Hence, if the probability of declaring a result significant when it is not (i.e., the "false positive rate") is fixed at $\alpha$ and all tests are independent, it follows that the probability of erroneously declaring one of p results significant when it is not increases to approximately $p\alpha$. The simplest way of correcting for this effect is to use the Bonferroni correction, which replaces the single-test significance level $\alpha$ with the more conservative p-test significance level $\alpha/p$. See P. WESTFALL AND S. YOUNG, RESAMPLING BASED MULTIPLE TESTING, Wiley, 1993.

Combining the Bonferroni correction with the Chebyshev inequality, we obtain the following conservative but simple, distribution-free significance threshold: a contingency lattice result is declared significant at the level $\alpha$ if the corresponding Chebyshev inequality result gives a probability less than $\alpha/p$. This approach gives the following bound on the magnitude of the z-scores:

$$\frac{1}{z^2} < \frac{\alpha}{p} \Rightarrow |z| > \sqrt{\frac{p}{\alpha}}. \quad (5)$$

That is, the subset size $N_{Rj}$ is declared significantly different from the comparison results $\{N_{ij}\}$ obtained from the M comparison datasets $\{D_i\}$ if $$\left|\frac{N_{Rj}-\hat{\mu}_j}{\hat{\sigma}_j}\right| > \sqrt{\frac{2^N-1}{\alpha}}, \quad (6)$$

where $\hat{\mu}_j$ is the mean of the sizes $\{N_{ij}\}$ for $i=1, 2, \ldots$ M and $\hat{\sigma}_j$ is the corresponding standard deviation, computed from Eqs. (2). For a three-way contingency lattice and a 5% nominal significance level $\alpha$, the z-score threshold appearing in Eqs. (5) and (6) is approximately $|z|>11:8$.

Note that all of the contingency lattice results summarized in Table 1 exceed this critical z-score, which indicates a significant association between rhabdomyolysis and all of the individual drugs, their pairs, and their three-way combinations. Subsequent investigation shows that the cause of these apparent associations is the large number of cases involving the drug Baycol present in each of these individual subsets. This effect—the spurious generation of association signals between a drug and an unrelated adverse event—is called a bystander effect and is a significant concern in the pharmacovigilance literature. See, for example, D. M. Coulter, A. Bate, E. H. B. Meyboom, M. Lindquist, and I. R. Edwards, *Antipsychotic drugs and heart muscle disorder in international pharmacovigilance: data mining study*, BRITISH MEDICAL JOURNAL, v 322, 1207-09 (2001).

5 Orthogonalized Contingency Lattices

A difficulty with the analysis described above is that subsets listing a particular drug or drug combination may also list other drugs or drug combinations with unknown frequencies. For example, the subset labeled "Plavix" in FIG. 2 contains all patient records that list the drug Plavix, regardless of whether they also list the drugs Baycol, Lopid, or both. Consequently, if there is a strong association between the drug Baycol and the condition rhabdomyolysis, which is known to be the case, and if there is a significant overlap between patient records listing Plavix and Baycol, then the apparent association between Plavix and rhabdomyolysis can be significantly inflated in the contingency lattice analysis just described. Note also that, even when using the multiway contingency tables, these bystander effects can be expected in traditional analyses based on contingency tables.

Figure 3:
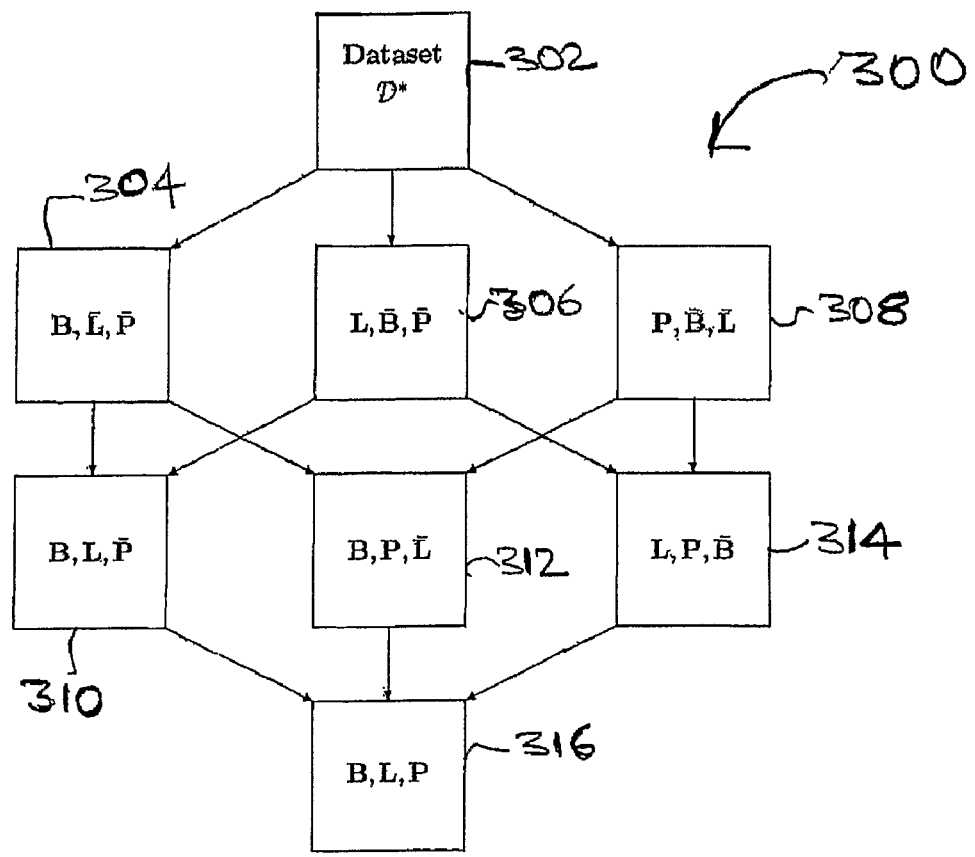
FIG. 3 is an exemplary orthogonal contingency lattice.

To overcome these bystander effects, in certain embodiments, the present invention provides orthogonalized contingency lattices as a basis for pharmacovigilance analysis. The basic idea is to replace subsets like "all patients taking Plavix" in the example considered earlier with non-overlapping subsets like "all patients taking Plavix but not taking either Baycol or Lopid." To illustrate this idea more completely, FIG. 3 shows the orthogonalized version 300 of the contingency lattice shown in FIG. 1. As before, the three drugs considered are designated as B (Baycol), L (Lopid), and P (Plavix), but in FIG. 3 an overbar is used to indicate that a certain condition is excluded in constructing the corresponding patient subset. For example, the left-most block 304 in the second row in FIG. 3 is designated B, $\overline{L}$, $\overline{P}$, defining the set of AERS ISR's listing the drug Baycol but not listing the drugs Lopid or Plavix. More generally, note that each of the seven subset blocks (304-316) appearing in FIG. 3 lists all three symbols B, L, and P, either without an overbar to indicate it is included in forming the subset, or with an overbar to indicate that it is excluded. As a consequence, it should be noted that all of these subsets are mutually exclusive, with no patient appearing in more than one subset.

The results obtained from the orthogonalized contingency lattice just described are analyzed exactly as in the case of the basic contingency lattice described previously. That is, the sizes of the subsets defined by the combinations of conditions of interest in the orthogonalized lattice are compared, between records satisfying the reference condition R and M randomly selected subsets of the same size that do not satisfy this reference condition. As discussed earlier herein, the comparison record set may also be a multiple or fraction of the size of the record set satisfying the reference condition provided the results from the comparison record set are suitably scaled so that comparisons effectively made between record sets of the same size.

Significant differences in subset size between those based on the reference condition and those based on the random comparison datasets give evidence of an association between the reference condition and the conditions of interest defining each subset in which the significant size difference has been observed. As before, significance is assessed using the Bonferroni-corrected z-score analysis described earlier herein. The primary difference between the results obtained with the original contingency lattice construction and those obtained with the orthogonalized construction lies in the fact that the orthogonalized patient subsets are mutually exclusive. Consequently, associations observed between the reference condition and the conditions of interest defining a subset cannot be a spurious consequence of associations between the reference condition and other conditions of interest, provided they are included in the orthogonalized contingency lattice. That is, spurious associations due to conditions not included in the analysis are still possible. For example, if Baycol were replaced with Lipitor in this example, the fact that many records listing Lopid also list Baycol would not enter into the analysis, so unrecognized Baycol-induced bystander effects would inflate the Lopid/rhabdomyolysis association, just as in the non-orthogonalized results presented in the preceding discussion.

Figure 4:
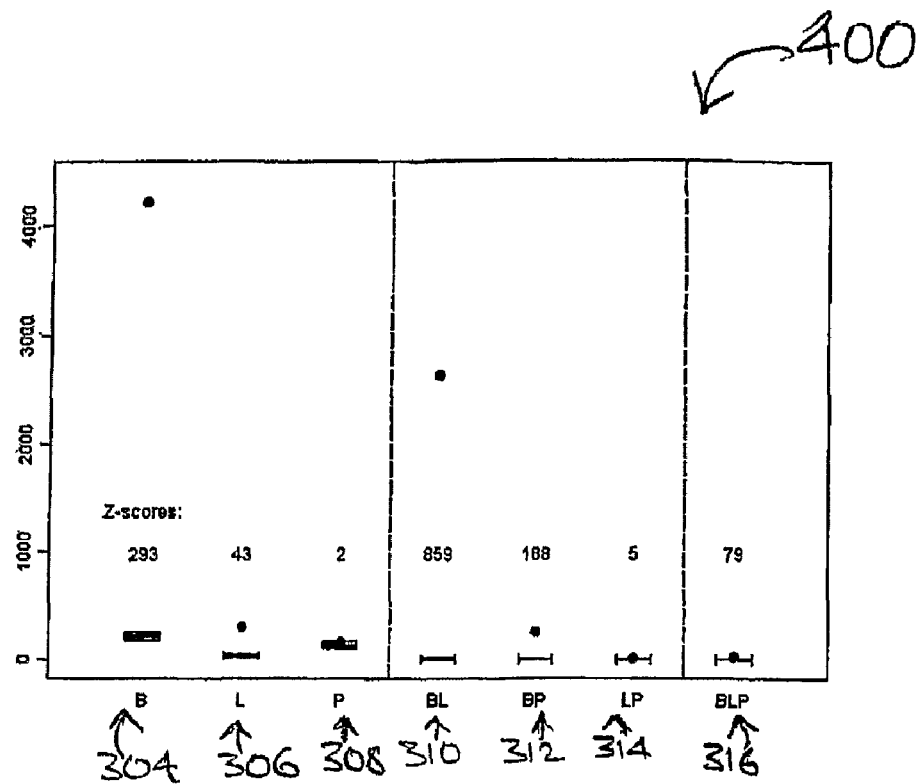
FIG. 4 is an exemplary boxplot that summarizes results from an orthogonal lattice in which the subset sizes obtained from randomized comparison sets are compared to the subset sizes for a reference condition from a reference dataset.

The orthogonalized contingency lattice results obtained for the example considered here are summarized in a boxplot 400 shown in FIG. 4, which should be compared with the boxplot 200 shown in FIG. 2. First, note the difference in horizontal scales between these two figures, reflecting the fact that the subsets (304-316) defining the orthogonalized lattice are generally smaller than the respective subsets (204-216) defining the original lattice. In particular, note that each of the subsets (304-316) indicated in FIG. 4 is contained in the corresponding subset (204-216) indicated in FIG. 2. For example, the subset designated B, $\overline{L}$, $\overline{P}$, in FIG. 4 is contained in the Baycol subset (Case B or 204) in FIG. 2. Second, and more significantly, note that the apparently strong association between Lopid and rhabdomyolysis implied by the results for Case L in FIG. 2 is much weaker in the orthogonalized results presented in FIG. 4. The magnitude of this difference is even more apparent from the z-scores presented in Table 2 below for the orthogonalized results, when compared with those presented in Table 1 for the original results. For the case of Lopid, it should be noted that removal of Baycol and Plavix records in the orthogonalized result decreases the z-score by an order of magnitude, from z=403 to z=43, increasing its associated probability by two orders of magnitude. Finally, the third major difference between these two figures is that the rhabdomyolysis result for Plavix (Case P), which falls clearly outside the range of the non-rhabdomyolysis results in the original analysis, falls within this range in the orthogonalized analysis. This difference is also reflected in the z-scores listed in Table 2: whereas in the original results, the association seen between Plavix and rhabdomyolysis was significant at the Bonferroni-corrected 5% level, this is no longer true for the orthogonalized results.

TABLE 2

Summary of subset definitions, sizes based on the rhabdomyolysis dataset, minimum and maximum subset sizes from the 200 randomly generated non-rhabdomyolysis datasets, the z-scores characterizing the differences between the rhabdomyolysis and non-rhabdomyolysis randomized datasets, and the corresponding probabilities derived from the Chebyshev inequality. These results correspond to the orthogonalized contingency lattice 400 shown in FIG. 4; with the z-scores marked with * are significant at the Bonferroni-corrected 5% significance level ($|z| > 12$).

| Case | $N_{rhabdo}$ | $N_{ref}^-$ | $N_{ref}^+$ | Z | $P_{Chebyshev}$ |
|---|---|---|---|---|---|
| B$\overline{LP}$ | 4204 | 186 | 257 | 293* | $1.17 \times 10^{-5}$ |
| L$\overline{BP}$ | 306 | 21 | 55 | 43* | $5.36 \times 10^{-4}$ |
| P$\overline{BL}$ | 163 | 109 | 169 | 2 | $2.20 \times 10^{-1}$ |
| BL$\overline{P}$ | 2634 | 2 | 21 | 859* | $1.36 \times 10^{-6}$ |
| B$\overline{L}$P | 260 | 0 | 6 | 187* | $2.83 \times 10^{-5}$ |
| LP$\overline{B}$ | 12 | 0 | 8 | 5 | $3.78 \times 10^{-2}$ |
| BLP | 30 | 0 | 2 | 79* | $1.58 \times 10^{-4}$ |

Comparing Tables 1 and 2, it should be noted that the z-scores associated with the orthogonalized results (Table 2) are, at least for this example, never larger in magnitude for the orthogonalized result with the corresponding non-orthogonalized original result (Table 1). In two cases, they are the same: one is the three-way interaction BLP where the subsets (116 and 316) are identical in the two contingency lattices, and the other is the interaction between Baycol and Lopid, where the subsets (110 and 310) differ in size (and content) by about 1%. Conversely, there are cases where the differences between these results are quite pronounced, most prominently in the case of Lopid (Case L or 106 vs. orthogonalized Case L$\overline{BP}$ or 306, where the z-score declines from 403 to 43. While the orthogonalized result remains significant, it is substantially less so, reflecting the fact that the orthogonalized Lopid subset is substantially smaller than the non-orthogonalized one (306 records vs. 2982 records). Finally, two other cases where the orthogonalization makes an important difference are those of Plavix alone and Plavix with Lopid: both original results are significant at the Bonferroni-corrected 5%, while the orthogonalized results are not. These last three differences—for Lopid, Plavix, and their combination—are a direct consequence of the Baycol bystander effect. Specifically, the subsets (106, 108, and 114) for these cases in the original contingency lattice all contain a significant fraction of records that also list the drug Baycol, while the corresponding subsets (306, 308, and 314) in the orthogonalized lattice do not. For example, 2,982 of the 11,773 rhabdomyolysis records list the drug Lopid, while all but 318 of these (~89%) also list Baycol.

TABLE 3

Comparative subset rankings for the original and orthogonalized contingency lattice results for Baycol, Lopid, and Plavix with respect to the adverse event rhabdomyolysis.

| Original Rank | Orthog. Rank | Original Subset | Orthog. Subset | Original z-score | Orthog. z-score |
|---|---|---|---|---|---|
| 1 | 1 | BL | BL$\overline{P}$ | 859* | 859* |
| 2 | 2 | B | B$\overline{LP}$ | 498* | 293* |
| 3 | 5 | L | L$\overline{BP}$ | 403* | 43* |
| 4 | 3 | BP | BP$\overline{L}$ | 200* | 187* |
| 5 | 4 | BLP | BLP | 79* | 79* |
| 6 | 7 | P | P$\overline{BL}$ | 26* | 2 |
| 7 | 6 | LP | LP$\overline{B}$ | 22* | 5 |

Table 3 ranks both the original contingency lattice subsets and the corresponding orthogonalized subsets by z-score. In both cases, the Baycol/Lopid set ranks first with a huge z-score of approximately 859, consistent with the strong association between this drug pair and rhabdomyolysis that was cited in the FDA's announcement of the Baycol withdrawal. Baycol alone ranks second in both cases, but the z-score for the orthogonalized result is substantially smaller than that for the original result (293 vs. 498), reflecting the large number of records listing Baycol that also list Lopid. The third-ranked subset differs substantially between the orthogonalized and original lattice results: for the original results, Lopid by itself ranked third, while in the orthogonalized results, this subset drops to fifth and the combination BPL̄ is ranked third. This result suggests a possible Baycol/Plavix/rhabdomyolysis association, stronger than any direct Lopid/rhabdomyolysis association.

Overall, the rankings based on the orthogonalized contingency lattice summarized in Table 3 suggest the following interpretation:

1. the strongest association between rhabdomyolysis and any of the drug combinations considered is that with Baycol and Lopid together, consistent with this well-known, harmful drug interaction;
2. all of the top four associations with rhabdomyolysis involve Baycol, either alone or together with one or both of the other two drugs considered;
3. there is only weak evidence in support an association between Lopid and rhabdomyolysis in the absence of Baycol;
4. there is no evidence in support of an association between Plavix and rhabdomyolysis in the absence of Baycol.

The orthogonalized lattice analysis approach described here can provide an extremely useful method for dealing with two important problems in pharmacovigilance: the treatment of multi-way interactions (e.g., drug-drug-drug, drug-drug-reaction, drug-drug-gender-age, etc.), and the treatment of bystander effects. A basic description of an example approach of an embodiment of the invention illustrates a well-known case: that of Baycol, where significant association with rhabdomyolysis, particularly when co-prescribed with Lopid, led to its withdrawal from the market. The technique is fairly simple and very broadly applicable, so it would applicable to a number of other examples and problem types, including:

1. explicit selection of reference conditions and/or conditions of interest on the basis of results obtained from pharmacovigilance volcano plots;
2. extension beyond drugs/adverse events to other types of conditions of interest, such as:
   a. gender,
   b. age group (e.g., age 65 years or older),
   c. AERS report types (e.g., Direct, Expedited, or Periodic)
   d. AERS report sources (e.g., health professional, foreign, etc.)
   e. AERS outcomes (e.g., death, hospitalization, etc.)
3. application to the analysis of patterns of missing data;
4. application to other clinical data analysis problems besides pharmacovigilance (e.g., characterization of Stratification and Synchronization Inference Technology (S SIFT) patient clusters on the basis of categorical variables, or detection of unusual features in registry data).

It should be noted that the methods described here may have a significant advantage in computational efficiency over other methods for examining the statistical significance of N-way interactions. In particular, this method generates and examines fixed-sized samples, and does not require examination of every record in the entire data set for each of the $2^N$ combinations of factors.

It should be noted that the specific examples discussed herein with respect to medical data discloses interactions caused by one or more drugs. However, it should be understood that interactions caused by one or more of drugs, medications, vaccines, or medical devices could be analyzed equally well using the techniques disclosed herein.

6 Code Descriptions

These subsections describe the S-plus procedures used to generate the results presented in the specific embodiments disclosed herein. The code disclosed herein is exemplary only and one skilled in the art would recognize various alternatives and modifications all of which are considered a part of the present invention. Specifically, Sec. 6.1 below describes the two simple ISR retrieval utilities used to construct the record index sequences on which all results are based. Routines to construct the basic three-way contingency lattice under the reference condition and the random comparison lattices are described in Sec. 6.2, and the corresponding routines used to generate the orthogonalized lattice results are described in Sec. 6.3.

6.1 ISR Utilities

Both the basic contingency lattices and the orthogonalized contingency lattices considered here are constructed from sequences of record indices that define both the reference condition and the conditions of interest on which these lattices are based. In the examples considered here, the reference condition corresponds to a collection of AERS Individual Safety Reports (ISR's) listing the adverse event "rhabdomyolysis," which is a MedDRA Preferred Term (PT). The S-plus procedure isrreacs constructs this ISR sequence from the adverse event (assumed to be a MedDRA PT in the AERS REAC dataset). The code for this routine is:

```
isrreacs <- function(ptname){
    ptnames <- REAC$PT
    isrs <- REAC$ISR
    ixptname <- which(casefold(ptnames) == casefold(ptname))
    unique(isrs[ixptname])
}
```

To generate the random comparison datasets, the logical complement of the index sequence generated by isrreacs is needed. This sequence is easily constructed as follows:

>isrref<-isrreacs(ptname)>

>israll<-unique(DEMO$ISR)>

>isrcomp<-setdiff(israll,isrref)

Here, israll is the sequence of all unique ISR's listed in the AERS demographic file DEMO, isrref is the sequence of ISR's satisfying the reference condition, and isrcomp is the sequence of ISR's not satisfying the reference condition.

The conditions of interest in the example considered here all correspond to the presence of drugs in the AERS ISR'S, and the sequences are generated analogously to the reference ISR sequences just described. Specifically, the ISR sequence for a condition of interest defined by a drug specified by bestdrug-name (from the corresponding field of the AERS drug file DRUG) is constructed by procedure isrdrugs. The code for this procedure is listed in Table 4.

TABLE 4

Code listing for S-plus procedure isrdrugs.

```
isrdrugs <- function(bestname){
    bnames <- DRUG$DRUGNAME.BEST
    isrs <- DRUG$ISR
    ixbname <- which(casefold(bnames) == casefold(bestname))
    unique(isrs[ixbname])
}
```

TABLE 5

Code listing for S-plus procedure lattice3cgen.

```
lattice3cgen <- function(isr0,isr1,isr2,isr3){
    numvec <- vector("numeric",8)
    numvec[1] <- length(isr0)
    isr1a <- intersect(isr0, isr1)
    numvec[2] <- length(isr1a)
    isr2a <- intersect(isr0, isr2)
    numvec[3] <- length(isr2a)
    isr3a <- intersect(isr0, isr3)
    numvec[4] <- length(isr3a)
    isr12 <- intersect(isr1a, isr2a)
    numvec[5] <- length(isr12)
    isr13 <- intersect(isr1a, isr3a)
    numvec[6] <- length(isr13)
    isr23 <- intersect(isr2a, isr3a)
    numvec[7] <- length(isr23)
    isr123 <- intersect(isr12, isr13)
    numvec[8] <- length(isr123)
    numvec
}
```

6.2 Contingency Lattice Routines

The procedure used to construct the basic three-way contingency lattice discussed in this note is lattice3cgen, listed in Table 5. This routine is called with the index sequence isr0 for the reference condition and the index sequences isr1, isr2, and isr3 for the three conditions of interest used in constructing the lattice. The result is a vector of length 8, whose first element contains the size $N_R$ of the reference dataset and whose second through eighth elements contain the sizes $N_{Rj}$ of the corresponding lattice subsets for j=1 (element 2) through j=7 (element 8).

The M random comparison lattices used to assess the significance of the contingency lattice characterized in procedure lattice3cgen are generated and characterized by procedure lattice3cran. This procedure is listed in Table 6

TABLE 6

Code for the S-plus procedure lattice3cran.

```
lattice3cran <- function(isr0,isr1,isr2,isr3,iseed,m,n){
    set.seed(iseed)
    omat <- matrix(nrow=m,ncol=8)
    for (i in 1:m){
        isr00 <- sample(isr0,size=n,replace=F)
        omat[i,] <- lattice3cgen(isr00,isr1,isr2,isr3)
    }
    omat
}
``` and is called with the logical complement of the isrreference sequence (isr0), with the reference sequences for the three conditions of interest from which the lattice is constructed (isr1, isr2, and isr3), with a seed (iseed) for the random number generator used to construct random data subsets, with the number of random subsets to generate (m), and with the number $N_R$ of records in the reference dataset (n in the calling sequence). Note that the passing parameter isr0 for this sequence is the complement of the passing parameter isr0 used to invoke procedure lattice3cgen, constructed as discussed in Sec. 6.1. The result returned by procedure lattice3cran is a matrix of dimensions M×8, where the first column contains the size $N_R$ of the reference dataset and all randomly generated comparison sets, and columns 2 through 8 contain the sizes $N_{ij}$ of the M collections of random subsets defining each comparison lattice.

6.3 Orthogonalized Lattice Routines

The procedures used in the orthogonalized contingency lattice analysis are orthogset3gen and orthog3cran, analogous to the basic contingency lattice procedures lattice3cgen and lattice3cran, respectively. Routine orthogset3gen is listed in Table 7 and its calling parameters and the format of its results are exactly the same as those for procedure lattice3cgen described in Sec. 6.2. Similarly, routine orthog3cran is listed in Table 8 and its calling parameters and the format of its results are exactly the same as those for procedure lattice3cran.

7 Two-Way Interaction Analysis

The orthogonalized lattice approach described herein may eliminate first-order and intermediate bystander effects, along with some weak second-order bystander effects. However, orthogonalized lattice analysis may still be susceptible to strong second-order bystander effects. The following paragraphs describe a two-way interaction analysis that may separate pure interactions from second-order bystander effects for the case of two drugs.

For example, consider two drugs, Drug A and Drug B, and assume that the question of interest is whether either or both are significantly associated with Adverse Reaction X. The essential idea behind the displays considered here is that they compare the numbers of times Adverse Reaction X is observed under the following four conditions: (1) among records listing both Drug A and Drug B; (2) among records listing Drug A without Drug B; (3) among records listing Drug B without Drug A; (4) among records listing neither Drug A nor Drug B.

In the following description, let N denote the size of the first subset listed above—i.e., the total number of records in the available database listing both drugs. The interaction analysis considered here begins by computing $N_X$, the number of times that Reaction X appears in this first record subset, and the objective of the analysis is to provide reference numbers to answer the following questions:

Is $N_X$ large (or small) compared to the number of times Reaction X appears in samples of size N listing Drug A alone?

Is $N_X$ large (or small) compared to the number of times Reaction X appears in samples of size N listing Drug B alone?

Is $N_X$ large (or small) compared to the number of times Reaction X appears in samples of size N listing neither Drug A nor Drug B?

Each of these questions defines a collection of random reference sets that may be used to provide answers. Specifically, M random samples, each of size N, are drawn from the reference population defined by each of these questions (i.e., Drug A alone, Drug B alone, and neither drug), and the number of records in each random sample that also lists Reaction X is recorded. Side-by-side boxplot displays provide a useful visualization of these results.

Figure 5:
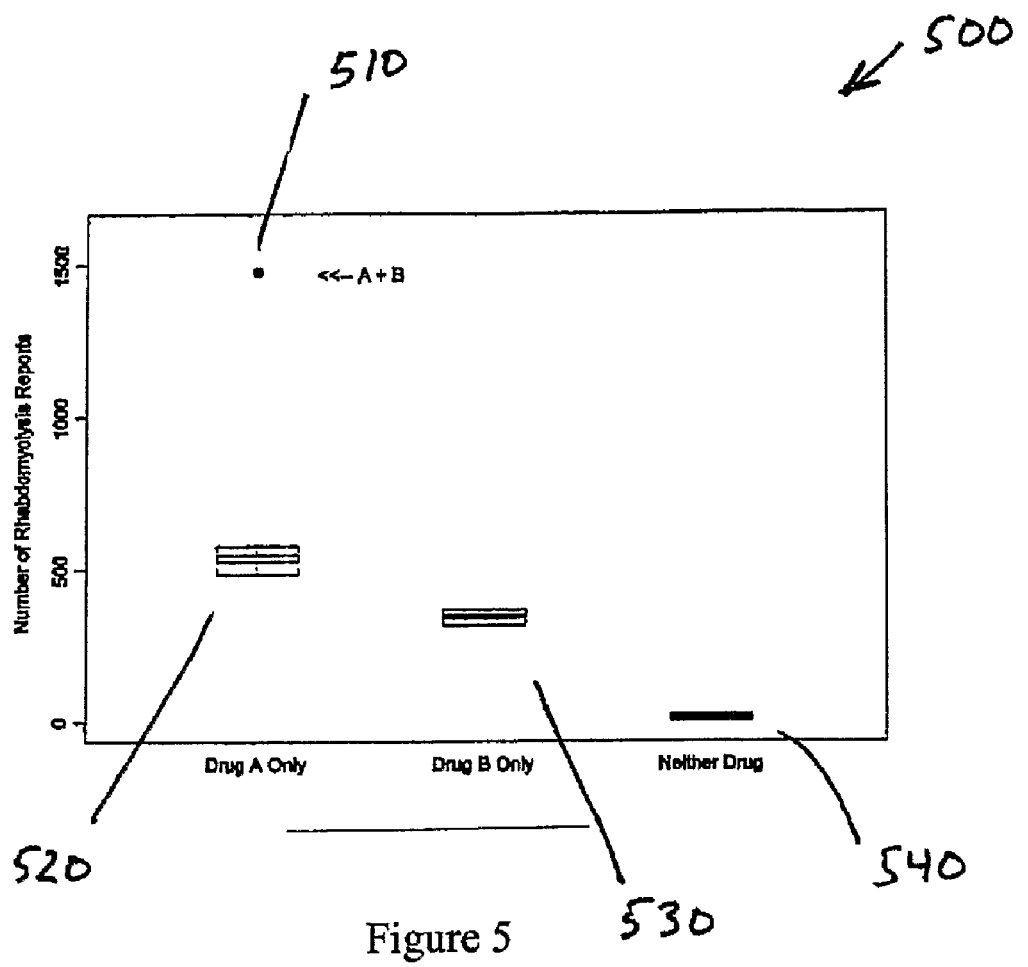
FIG. 5 is an exemplary boxplot that summarizes results from a two-way interaction analysis showing a strong evidence of an interaction between Drug A and Drug B.

As a specific example, FIG. 5 presents the boxplot 500 results obtained for the drugs Baycol and Lopid, with the adverse event "rhabdomyolysis." The solid circle 510 in FIG. 5 represents the number $N_X$ of records listing rhabdomyolysis in the N=1728 records listing both Baycol and Lopid. The left-most boxplot 520 summarizes the range of results obtained for the drug Baycol alone, giving the number of records in 100 random samples, each of size N=1728 that list the adverse event rhabdomyolysis and the drug Baycol but not the drug Lopid. The central boxplot 530 summarizes the range of results obtained for the drug Lopid alone, computed analogously, and the right-most boxplot 540 summarizes the range of results obtained from 100 random samples drawn from those records that list neither drug. The fact that the solid circle 510 lies so far above the range of variation of any of the three reference boxplots provides strong evidence of an interaction between the two drugs: the adverse reaction rhabdomyolysis is much more likely in patients taking both drugs than in patients taking either drug alone. In fact, this interaction was cited explicitly in the FDA's withdrawal notice for the drug Baycol.

Figure 6:
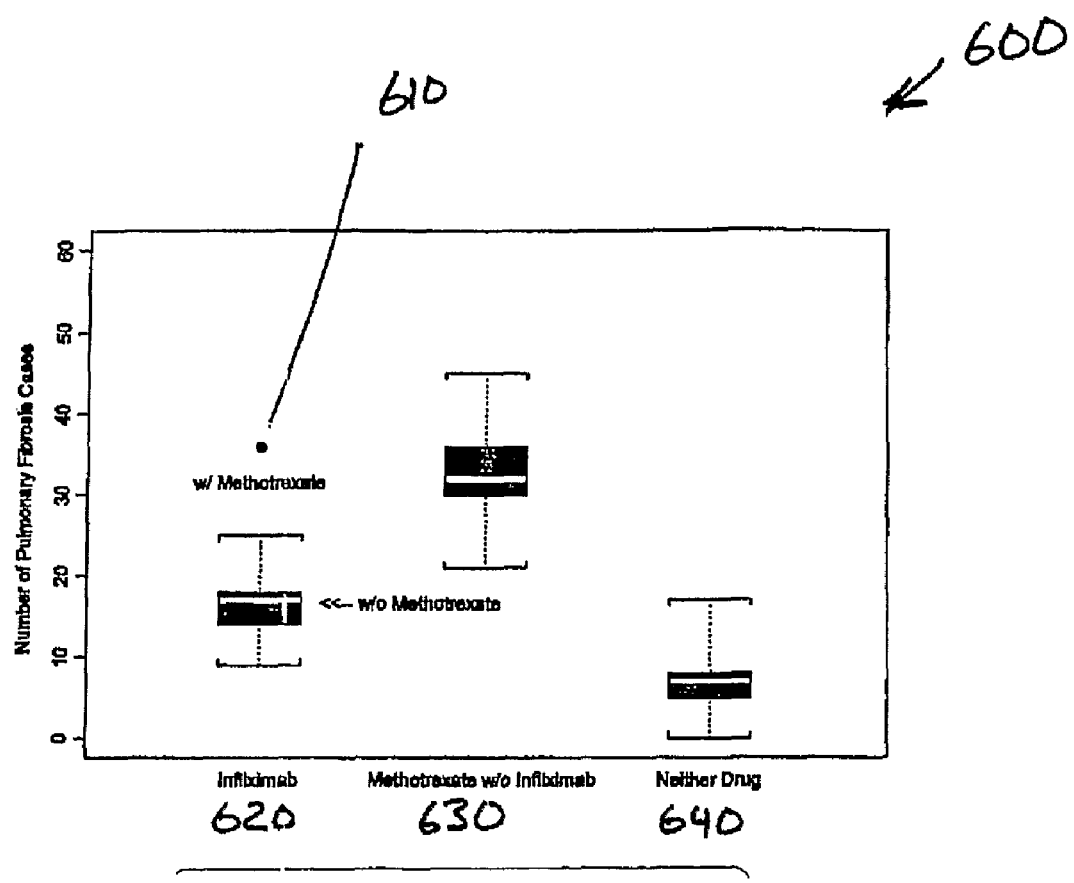
FIG. 6 is an exemplary boxplot that summarizes results from a two-way interaction analysis showing a second order bystander effect.

FIG. 6 presents analogous boxplot 600 results to those just described, but for the drugs Infliximab and Methotrexate, in conjunction with the adverse event "pulmonary fibrosis." As in the previous example, the solid circle 610 represents the number of records listing the adverse event in combination with both drugs, while the boxplots 620, 630, 640 summarize the numbers of times the adverse event appears in 100 random samples drawn from each of the three reference populations: records listing the drug Infliximab but not Methotrexate, records listing the drug Methotrexate but not Infliximab, and records listing neither drug. Here, the fact that the solid circle 610 lies well above the range of variation seen for the drug Infliximab alone suggests the possibility of a drug interaction, but the fact that this point lies well within the range of variation seen for the drug Methotrexate alone indicates this to be a second-order bystander effect. Specifically, these results imply that it is the association between "pulmonary fibrosis" and the drug Methotrexate that is responsible for the large number of cases seen when both drugs are present, rather than a drug interaction effect like that seen for Baycol and Lopid in the previous example.

8 Augmented Lattice Displays

The augmented lattice display approach may be used to address strong second-order bystander effects involving more than two medical products or conditions. An augmented lattice display combines the results obtained from the orthogonalized lattice described herein with the two-way interaction analysis procedure described herein. This display includes the same individual points and reference boxplots as in the orthogonalized lattice, augmenting the plot for any results that are declared significant but which may represent second-order bystander effects. If Drug A exhibits a strong association with the adverse event under consideration, records listing Drug A along with other drugs should have a significant probability of listing the adverse event even in the absence of any effect from the other drugs, as seen in the example of Infliximab and Methotrexate shown in FIG. 6. Thus, the augmented lattice display includes an estimate of the range of values expected for the drug combination in the absence of any interaction effects. If the observed result falls significantly above this range, this observation provides evidence for a positive (e.g., harmful) interaction involving Drug A, while if the observed result falls significantly below this range, this observation provides evidence for a negative (e.g., beneficial) interaction involving Drug A. Results falling within this range suggest that drug interaction effects are not significant.

The point in the orthogonalized lattice plot corresponds to $N_X$, the number of times a specified drug combination appears among those records listing Adverse Reaction X. An equivalent interpretation of $N_X$, however, is as the number of times Reaction X appears in the set of N records listing the specified drug combination. This alternative view provides the basis for the augmented reference values considered here, which are the numbers of times Reaction X appears in M random samples, each of size N, drawn from records listing Drug A alone, without the other drugs included in the combination. The basic idea is that if these other drugs have no interaction effects, the observed value of $N_X$ should fall within the range of these random samples.

The drug infliximab (Remicade) is indicated for treatment of arthritis and Crohn's disease. The first 25 of 365 adverse events for this drug that exceed the Bonferroni-corrected 5% significance threshold, ranked in descending order of Statistical Unexpectedness, are listed in Table 7. The strongest association seen in this list is that with "tuberculosis nos," consistent with the black box warning issued in October of 2001, which included the following wording: Tuberculosis (frequently disseminated or extrapulmonary at clinical presentation), invasive fungal infections, and other opportunistic infections, have been observed in patients receiving Remicade. Some of these infections have been fatal. Altogether, the 12 distinct tuberculosis designations listed in Table 7 fall above the Bonferroni-corrected 5% Statistical Unexpectedness limit and are combined here into the overall tuberculosis adverse reaction used in subsequent discussions. Further examination of the AERS ISR's associated with both the drug infliximab and the tuberculosis reactions listed in Table 7 shows that infliximab is frequently co-prescribed with the corticosteroids prednisone or prednisolone, with methotrexate, or with leflunomide. These observations motivate the interaction analysis described here, which attempts to determine which of these drugs or drug combinations are strongly associated with tuberculosis.

TABLE 7

Listing of the top 25 adverse events associated with the drug infliximab, ranked in descending order of Statistical Unexpectedness.

| No. | Reaction | $R_{AB}$ | $\log_{10} U_{AB}$ | $N_B$ | $N_{AB}$ |
|---|---|---|---|---|---|
| 1 | tuberculosis nos | 29.00 | >308.00 | 413 | 275 |
| 2 | lupus-like syndrome | 27.45 | 215.11 | 284 | 179 |
| 3 | systemic lupus erythematosus | 11.24 | 137.84 | 744 | 192 |
| 4 | disseminated tuberculosis | 30.00 | 117.79 | 135 | 93 |
| 5 | pulmonary tuberculosis | 23.31 | 109.04 | 185 | 99 |
| 6 | basal cell carcinoma | 21.17 | 92.07 | 181 | 88 |
| 7 | flushing | 4.37 | 83.41 | 2530 | 254 |
| 8 | medication error | 0.07 | 75.78 | 9970 | 17 |
| 9 | tuberculosis | 25.34 | 74.07 | 110 | 64 |
| 10 | pneumonia nos | 2.92 | 71.42 | 5508 | 369 |
| 11 | dna antibody nos positive | 24.01 | 66.39 | 107 | 59 |
| 12 | infusion related reaction | 19.32 | 62.93 | 142 | 63 |
| 13 | sepsis nos | 3.28 | 61.87 | 3553 | 268 |
| 14 | rhabdomyolysis | 0.08 | 58.33 | 7783 | 14 |
| 15 | listeriosis | 30.26 | 52.60 | 59 | 41 |
| 16 | antinuclear antibody positive | 12.93 | 51.53 | 219 | 65 |
| 17 | crohn's disease aggravated | 22.02 | 48.51 | 89 | 45 |
| 18 | rheumatoid arthritis aggravated | 12.27 | 46.14 | 213 | 60 |
| 19 | drug withdrawal syndrome | 0.02 | 44.68 | 4782 | 2 |

TABLE 7-continued

Listing of the top 25 adverse events associated with the drug infliximab, ranked in descending order of Statistical Unexpectedness.

| No. | Reaction | $R_{AB}$ | $\log_{10} U_{AB}$ | $N_B$ | $N_{AB}$ |
|---|---|---|---|---|---|
| 20 | crohn's disease | 11.26 | 43.74 | 232 | 60 |
| 21 | pneumocystis carinii pneumonia | 9.58 | 43.17 | 300 | 66 |
| 22 | histoplasmosis nos | 28.47 | 42.29 | 52 | 34 |
| 23 | rigors | 2.65 | 41.86 | 4136 | 252 |
| 24 | pharmaceutical product complaint | 0.05 | 41.69 | 5060 | 6 |
| 25 | pyrexia | 1.80 | 41.44 | 14387 | 596 |

TABLE 8

Listing of the 12 distinct versions of tuberculosis included in the combined adverse event "tuberculosis" considered in association with the drug infliximab.

| No. | Designation | $U_{ab}$ |
|---|---|---|
| 1 | tuberculosis nos | $>10^{308}$ |
| 2 | disseminated tuberculosis | $6.22 \times 10^{117}$ |
| 3 | pulmonary tuberculosis | $1.11 \times 10^{109}$ |
| 4 | tuberculosis | $1.18 \times 10^{74}$ |
| 5 | lymph node tuberculosis nos | $4.98 \times 10^{15}$ |
| 6 | spleen tuberculosis | $1.47 \times 10^{12}$ |
| 7 | tuberculosis gastrointestinal nos | $2.85 \times 10^{10}$ |
| 8 | peritoneal tuberculosis | $8.61 \times 10^{9}$ |
| 9 | lymph node tuberculosis | $1.57 \times 10^{8}$ |
| 10 | tuberculosis reactivated | $3.40 \times 10^{6}$ |
| 11 | bone amp joint tuberculosis | $1.34 \times 10^{6}$ |
| 12 | bone & joint tuberculosis | $1.09 \times 10^{5}$ |

In this case, N=898 patients exhibit one or more of the 12 forms of tuberculosis listed in Table 8, and the subsets defining the contingency lattice correspond to subsets of these patients who are taking each of the fifteen possible combinations of one or more of these drugs, numbered as defined in Table 9.

TABLE 9

The fifteen combinations of the four drugs considered here for their association with tuberculosis: infliximab, steroids (either prednisone or prednisolone), methotrexate, and leflunomide.

| No. | Drug or combination |
|---|---|
| 1 | infliximab |
| 2 | steroids (either prednisone or prednisolone) |
| 3 | methotrexate |
| 4 | leflunomide |
| 5 | infliximab and steroids |
| 6 | infliximab and methotrexate |
| 7 | infliximab and leflunomide |
| 8 | steroids and methotrexate |
| 9 | steroids and leflunomide |
| 10 | methotrexate and leflunomide |
| 11 | infliximab, steroids, and methotrexate |
| 12 | infliximab, steroids, and leflunomide |
| 13 | infliximab, methotrexate, and leflunomide |
| 14 | steroids, methotrexate, and leflunomide |
| 15 | infliximab, steroids, methotrexate, and leflunomide |

Figure 7:
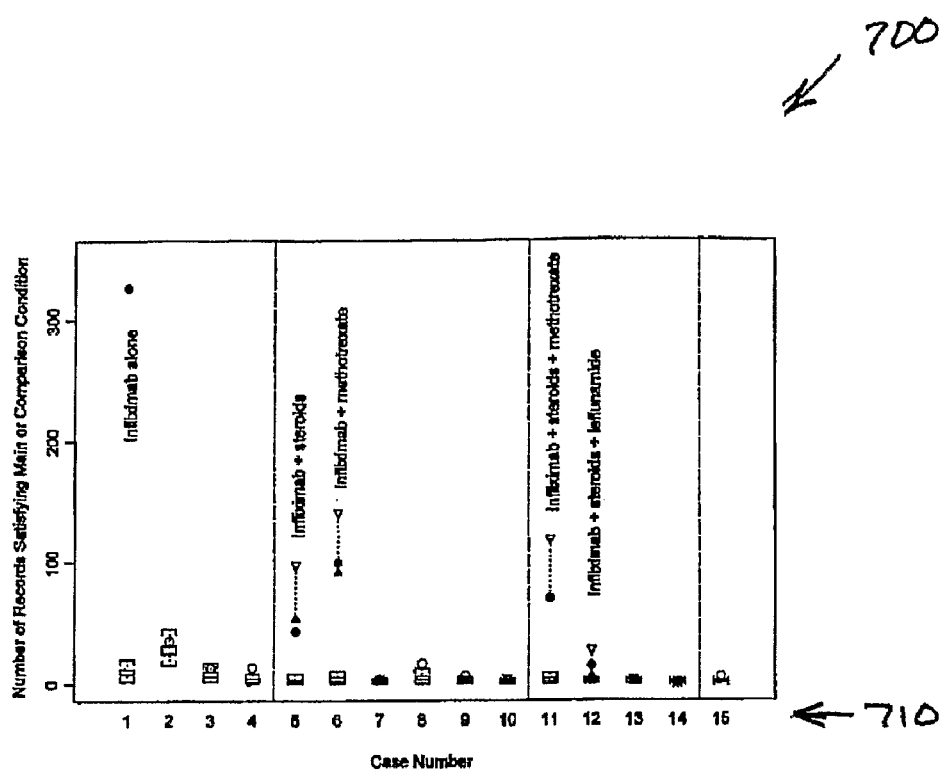
FIG. 7 is an exemplary boxplot that summarizes results from an augmented lattice display approach involving potential interactions between four medical products.

FIG. 7 provides an illustration 700 of the results of cases 710 as described in Table 9. The points (represented as either open or closed circles) in FIG. 7 correspond to the numbers of patients in each of these subsets who report tuberculosis. To provide a basis for comparison, the boxplots in FIG. 7 describe the ranges of the corresponding subset sizes seen in 200 random samples of patients who do not list any of the 12 forms of tuberculosis considered here. Points lying significantly above the range of the boxplots provide evidence of positive associations, while points lying significantly below the range of the boxplots provide evidence of negative associations.

The question of what constitutes "significantly above" or "significantly below" is decided as follows. First, the z-score for each point relative to its associated boxplot is defined as:

$$z = \frac{x - \mu}{\sigma}, \tag{3}$$

where x is the number of times the drug or drug combination defining the subset appears among records listing the adverse reaction, μ is the average of the numbers of times this drug or drug combination appears in each of the random reference samples, and σ is the standard deviation of these numbers. The probability of observing a given z-score decreases with its magnitude and depends on the underlying distribution of the random reference data, which is unknown. Under the very weak assumption that this distribution has finite variance, however, the Chebyshev bound implies that $$P\{|z| > t\} \leq \frac{1}{t^2}. \tag{4}$$

Based on this observation, x is declared unusually large if $z > 1/\sqrt{p}$ where p is a standard probability threshold, and unusually small if $z < -1/\sqrt{p}$. The results presented here adopt the standard 5% significance threshold, p=0.05.

One more refinement is needed, however, to account for the fact that FIG. 7 does not represent a single comparison, but rather M=15 comparisons. For statistically independent comparisons, we would expect that M comparisons, each having a probability p of making an error individually, would have a probability on the order of Mp of making at least one error. To overcome this problem, the Bonferroni correction is adopted, which simply divides the probability threshold value p by the number of comparisons M so that the overall probability of making at least one error is again p. This correction has the effect of increasing the z score magnitude threshold from $1/\sqrt{p}$ to $$t = 1/\sqrt{p/M} = \sqrt{\frac{M}{p}}. \tag{5}$$

In FIG. 7, points for which |z| exceeds this threshold are marked as solid circles, while points that do not exceed this threshold are marked as open circles. Interpreting these solid circles as evidence for significant associations with tuberculosis leads to the conclusion that the nine drugs or drug combinations labeled in FIG. 7 exhibit significant associations.

The points represent the number of times $N_X$ each drug or drug combination appears uniquely in records listing the adverse event tuberculosis. The five solid circles represent results that are declared significant by the orthogonalized lattice analysis, based on their distance from the corresponding reference boxplots appearing across the bottom of the figure. For each of the four significant multiple drug combinations involving infliximab (Cases 5, 6, 11, and 12), the associated range of 200 random reference values for $N_X$ is shown as a dashed vertical line between the minimum, represented by an open triangle, and the maximum, represented by an inverted open triangle. These reference values were computed as described above: each drug combination defines a set of size N consisting of all records listing the indicated drugs but not listing the excluded drugs. Then, 200 random samples of this size are drawn from the larger set of records listing only the drug infliximab and none of the other three, and the number of these records listing tuberculosis is determined. The reference ranges shown in the plot correspond to the ranges for these numbers.

In three of these cases—combinations of infliximab with methotrexate only, with both steroids and methotrexate, and with both steroids and leflunomide—the original $N_X$ value falls within this range of 200 random reference values. Thus, these three combinations represent second-order bystander effects since the range of $N_X$ values expected on the basis of the infliximab/tuberculosis association alone covers the observed $N_X$ value. In the one remaining case—Case 5, the combination of infliximab with steroids—the observed $N_X$ value falls slightly below the range of the random reference values, suggesting the possibility of a weak protective interaction between steroids and infliximab. Thus, the only strong positive association with tuberculosis is that with infliximab alone, as shown in FIG. 7.

9 Dependence on Demographic Variables

An extension of the two-way interaction analysis method described earlier may be used. The purpose of this extension is to provide a computationally-based tool that permit the assessment of the extent to which the association results, obtained by methods described in the literature, depend on demographic variables like age or gender that may be included in the data source on which the analysis is based. Given a specified drug and adverse event, this analysis method is based on four data subsets analogous to those used in the two-way analysis, namely: (1) records listing both the drug and the adverse event; (2) records listing the drug but not the adverse event; (3) records listing the adverse event but not the drug; (4) records listing neither the drug nor the adverse event.

These records are characterized in one of two ways. For continuous demographic variables like age or weight, each collection of records is characterized by the average of the available values for this demographic variable. In the illustrative embodiment described here, no imputation of missing values for this variable is performed, although doing so will be apparent to one skilled in the art upon review of this disclosure and could be accomplished by any one of several different methods that have been described in the literature. See, for example, R. J. A. Little and D. B. Rubin, *Statistical Analysis with Missing Data*, 2nd ed., Wiley, 2002, and R. K. Pearson, *Mining Imperfect Data*, SIAM, Philadelphia, 2005. For categorical demographic variables like gender or race, these collections of records are characterized by the fraction of records for which the variable assumes a specified value (e.g., "fraction of records listing male gender").

Given the four classes of records listed above and a numerical characterization like those just described for each record class, the analysis method proposed here proceeds as follows. First, the collection of records listing both the drug and the adverse event has a fixed size N, and the quantitative characterization just described yields a single number when applied to these N records. Next, a collection of M random samples, each of N records, is drawn from the collection of records from each of the other three classes: all records listing the drug but not the adverse event, all records listing the adverse event but not the drug, and all records listing neither the drug nor the adverse event. The quantitative characterization described above is then applied to each of these M random samples, yielding a collection of M numerical values for each of these three reference populations. A graphical display is then constructed to compare the original result with the M results from each reference population, exactly analogous to the two-way interaction analysis plots described earlier.

Figure 8:
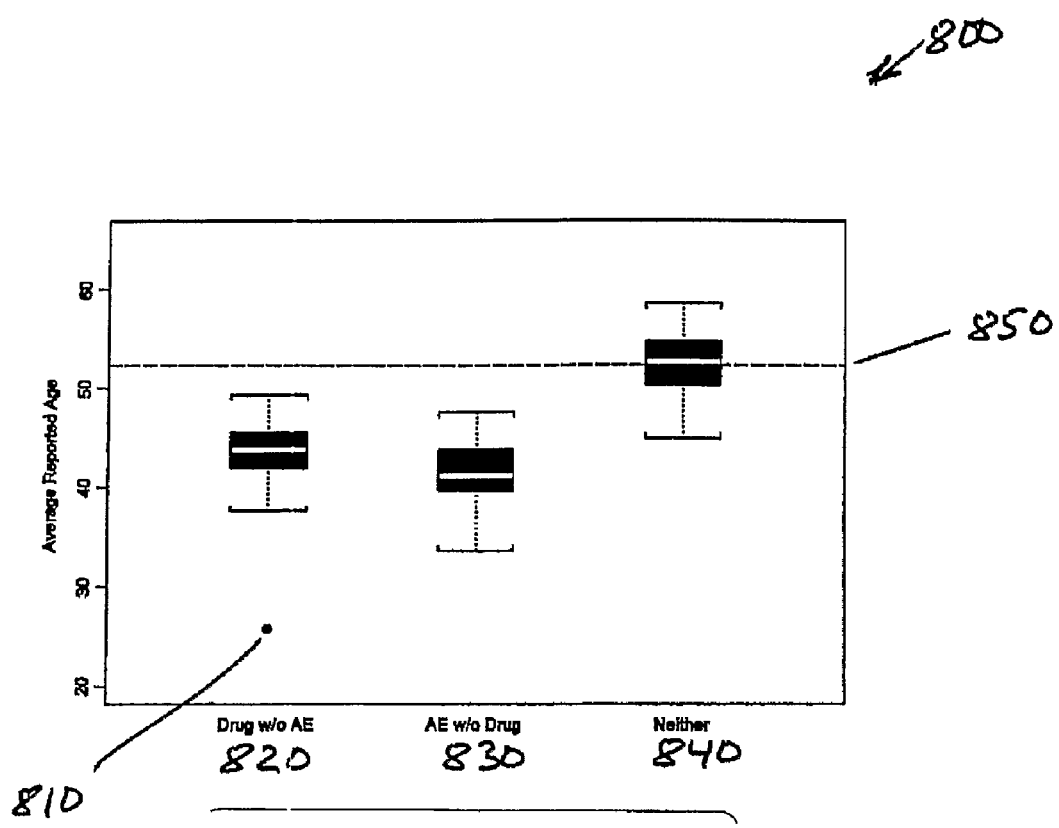
FIG. 8 is an exemplary boxplot that summarizes results from analysis of age as a demographic variable.

FIG. 8 illustrates via a boxplot 800 the use of the average age characterization described above for the drug Pseudoephedrine and the composite adverse event defined by either "convulsion" or "grand mal convulsion." The solid dot 810 represents the average reported age for N=67 records that list both the drug and the adverse event. The three boxplots summarize the average ages of M=100 independent random samples, each of size N=67 and each drawn from one of the three reference populations defined above. Specifically, the left-most boxplot 820 summarizes the average reported ages for records that list the drug Pseudoephedrine without either of the adverse reactions "convulsion" or "grand mal convulsion." The central boxplot 830 summarizes the average reported ages for records listing one or both of these adverse reactions but not listing the drug, and the right-most boxplot 840 summarizes the average reported ages for records listing neither the adverse event nor the drug. The dashed line 850 in the plot represents the average reported age for the subset of the AERS database from which these results were computed.

The results shown in FIG. 8 demonstrate first, that the average reported age for records listing both the drug and the adverse event are substantially lower than those for random samples from any of the three reference populations. This observation suggests that age may be an important factor in the association between this drug and adverse event. In particular, while it appears from FIG. 8 that the average reported ages for both records listing the drug alone and those listing the adverse event alone are significantly lower than average for the AERS database overall (specifically, note that the dashed line lies above the average age range for both of these populations), the average reported age for records listing both the drug and the adverse event lies well below the range of variation seen for either of these reference populations.

Figure 9:
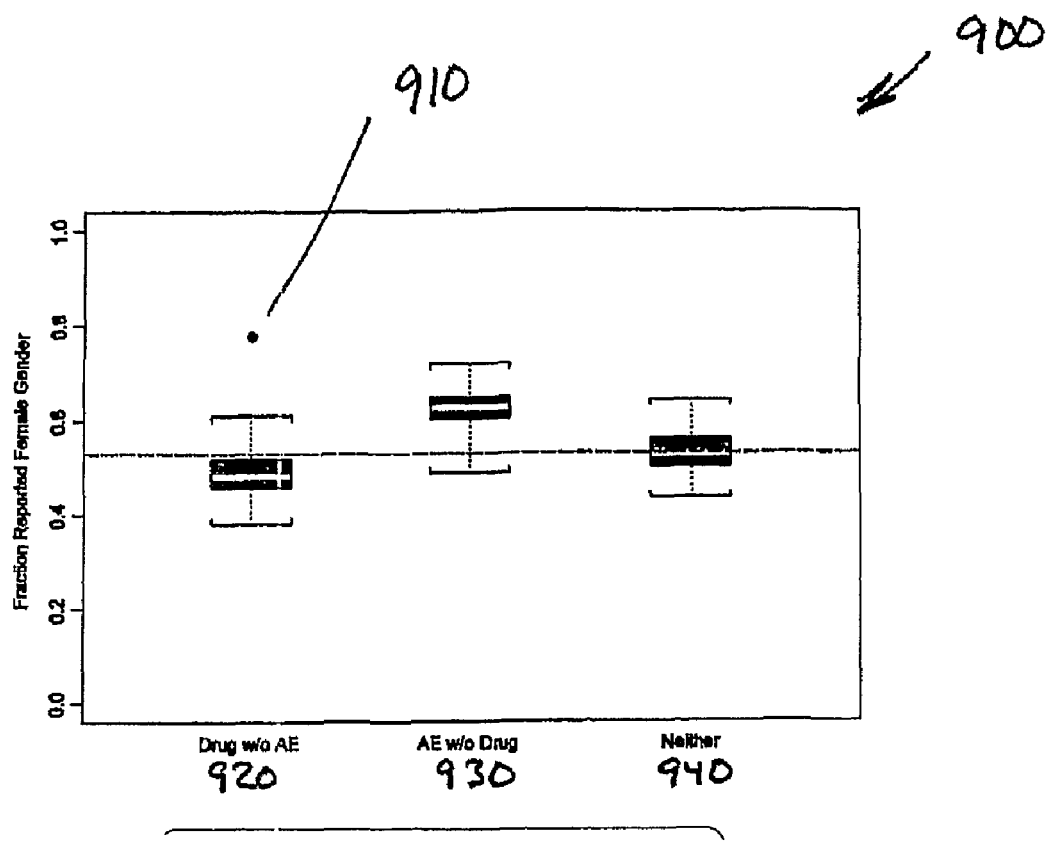
FIG. 9 is an exemplary boxplot that summarizes results from analysis of gender as a demographic variable.

As a second illustrative example, the boxplot 900 of FIG. 9 shows the analogous results obtained using the fraction of records listing gender as "female" for the combination of the drug Accutane with the adverse event "mood swings." Here, the solid circle 910 represents the fraction of the N records listing the drug Accutane and the adverse event "mood swings" that also list female gender. The three boxplots 920, 930, 940 in FIG. 9 give this characterization for the three reference populations analogous to those considered in the previous example: M=100 randomly drawn samples, each of size N, from records listing the drug Accutane without the adverse event, from those listing "mood swings" without the drug, and from those listing neither the drug nor the adverse event. Here, the fact that the solid circles lies above the range of all three boxplots means that the combination of the drug and the adverse event is significantly more likely to appear in a record listing female gender than is typical for any of the three reference populations. This observation suggests that gender may play a role in this drug/event association.

10 Generalized Computing System Implementation

Figure 10:
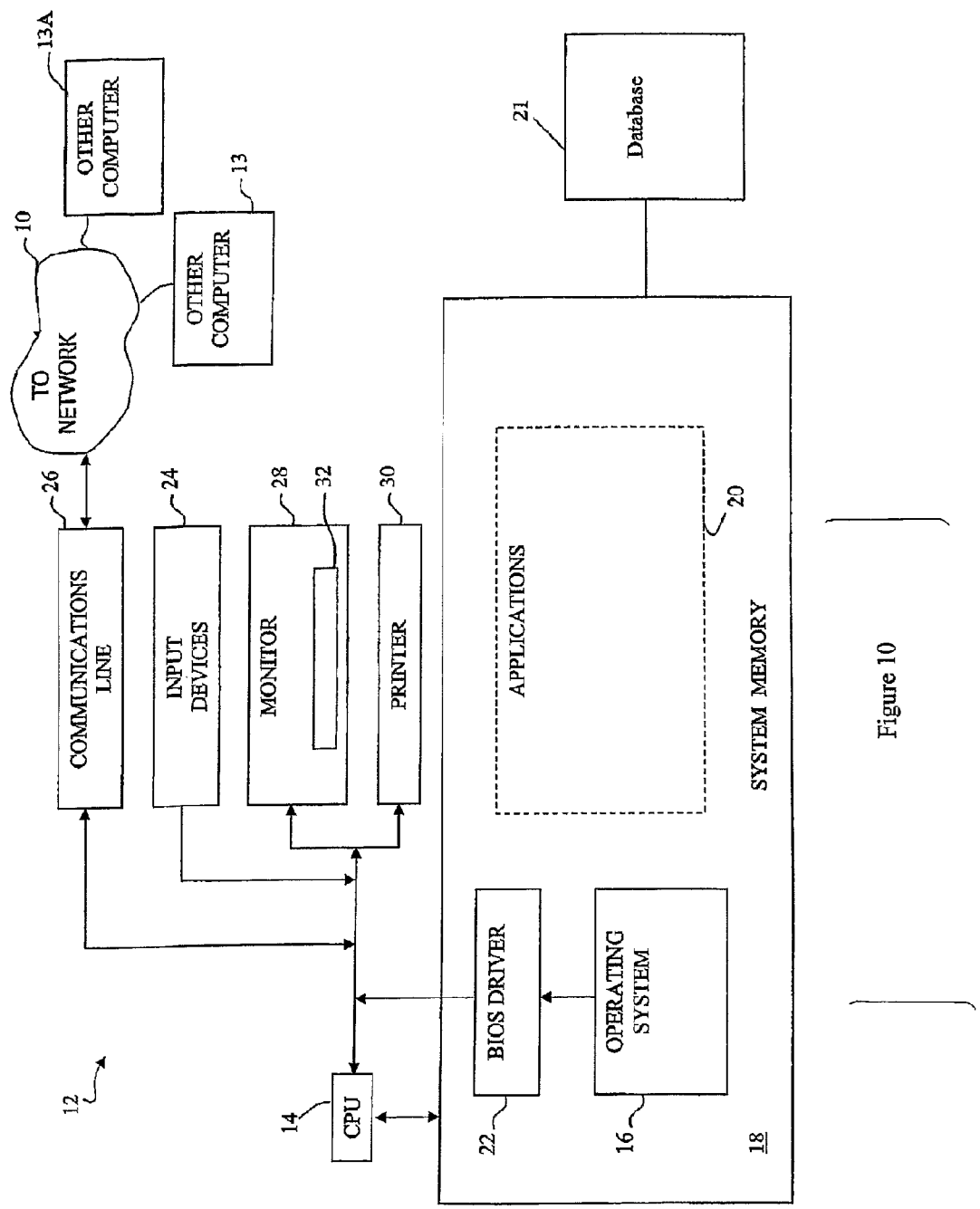
FIG. 10 is an exemplary computing system diagram in which the system and method of the present application may be implemented.

FIG. 10 illustrates the components of a generic computing system connected to a general purpose electronic network 10, such as a computer network. The computer network can be a virtual private network or a public network, such as the Internet. As shown in FIG. 10, the computer system 12 includes a central processing unit (CPU) 14 connected to a system memory 18. The system memory 18 typically contains an operating system 16, a BIOS driver 22, and application programs 20. In addition, the computer system 12 contains input devices 24 such as a mouse or a keyboard 32, and output devices such as a printer 30 and a display monitor 28, and a permanent data store, such as a database 21. The computer system generally includes a communications interface 26, such as an Ethernet card, to communicate to the electronic network 10. Other computer systems 13 and 13A also connect to the electronic network 10 which can be implemented as a Wide Area Network (WAN) or as an internetwork, such as the Internet. Data is stored either in many local repositories and synchronized with a central warehouse optimized for queries and for reporting, or is stored centrally in a dual use database.

One skilled in the art would recognize that the foregoing describes a typical computer system connected to an electronic network. It should be appreciated that many other similar configurations are within the abilities of one skilled in the art and it is contemplated that all of these configurations could be used with the methods and systems of the present invention. Furthermore, it should be appreciated that it is within the abilities of one skilled in the art to program and configure a networked computer system to implement the method steps of the present invention, discussed earlier herein. For example, such a computing system could be used to implement the method of evaluating interaction of two or more medical products or conditions using contingency lattices.

The present invention also contemplates providing computer readable data storage means with program code recorded thereon (i.e., software) for implementing the method steps described earlier herein. Programming the method steps discussed herein using custom and packaged software is within the abilities of those skilled in the art in view of the teachings and code fragments disclosed herein.

Other embodiments of the invention will be apparent to those skilled in the art from a consideration of the specification and the practice of the invention disclosed herein. It is intended that the specification be considered as exemplary only, with such other embodiments also being considered as a part of the invention in light of the specification and the features of the invention disclosed herein.

What is claimed is:

1. A computer implemented method of evaluating interaction of two or more medical products or conditions, in the context of a reference condition, based on a dataset of patient records, comprising:

developing a reference contingency lattice of reference lattice subsets from a subset of the patient records containing the reference condition, wherein each reference lattice subset corresponds to the patient records that contain the reference condition and that contain a respective medical product or condition, or combination of medical products or conditions, of the two or more medical products or conditions;

developing a plurality of comparison contingency lattices, each of the comparison contingency lattices developed from a respective random subset of the patient records not containing the reference condition, wherein each of the respective random subsets is of a same size as the subset of patient records containing the reference condition, and wherein each of the comparison contingency lattices includes comparison lattice subsets, wherein each comparison lattice subset is associated with a respective reference lattice subset and corresponds to the patient records containing the respective medical product or condition, or combination of medical products or conditions, of the associated reference lattice subset; and comparing, via a processor, the reference lattice subsets of the reference contingency lattice to the associated comparison lattice subsets of the comparison contingency lattices to determine a difference in one of the reference lattice subsets of the reference contingency lattice from the associated comparison lattice subsets of the comparison contingency lattices, wherein the difference is indicative of an interaction between the medical products or conditions with respect to the reference condition.

2. The method of claim 1, wherein the step of comparing the reference lattice subsets of the reference contingency lattice to the associated comparison lattice subsets of the comparison contingency lattices comprises calculating a z-score for at least one reference lattice subset of the reference contingency lattice based on the associated comparison lattice subsets in the comparison contingency lattices.

3. The method of claim 2, wherein a significance level of any of the z-scores is adjusted by a Bonferroni correction based on a plurality of comparisons.

4. The method of claim 1, wherein the medical products comprise drugs, medications or vaccines.

5. The method of claim 1, wherein the medical products comprise medical devices.

6. The method of claim 1, further comprising displaying the reference contingency lattice with subsets highlighted based on the indication of the interaction between the medical products or conditions.

7. The method of claim 1, wherein the reference contingency lattice and the comparison contingency lattices each comprise subsets having a partial order such that between any two subsets there exists a least upper bound subset and a greatest lower bound subset.

8. A computer implemented method of evaluating interaction of two or more medical products or conditions, in the context of a reference condition, based on a dataset of patient records, comprising:

developing a reference orthogonal contingency lattice of reference lattice subsets from a subset of the patient records containing the reference condition, wherein each reference lattice subset corresponds to the patient records that contain the reference condition and that contain a respective medical product or condition, or combination of medical products or conditions, of the two or more medical products or conditions, and wherein each reference lattice subset excludes the medical products or conditions, or combination of medical products or conditions, that correspond to other reference lattice subsets;

developing a plurality of comparison contingency lattices, each of the comparison contingency lattices developed from a respective random subset of the patient records not containing the reference condition, wherein each of the respective random subsets is of a same size as the subset of patient records containing the references condition, and wherein each of the comparison contingency lattices includes comparison lattice subsets, wherein each comparison lattice subset is associated with a respective reference lattice subset and corresponds to the patient records containing the respective medical product or condition, or the combination of medical products or conditions, of the associated reference lattice subset, and wherein each comparison lattice subset excludes the medical products or conditions, or combination of medical products or conditions, that correspond to the reference subsets with which the comparison lattice subset is not associated; and comparing, via a processor, the reference lattice subsets of the reference orthogonal contingency lattice to the associated comparison lattice subsets of the comparison contingency lattices to determine a difference in one of the reference lattice subsets of the reference orthogonal contingency lattice from the associated comparison lattice subsets of the comparison contingency lattices, wherein the difference is indicative of an interaction between the medical products or conditions with reference to the reference condition.

9. The method of claim 8, wherein the step of comparing the reference lattice subsets of the reference orthogonal contingency lattice to the associated comparison lattice subsets of the comparison contingency lattices comprises calculating a z-score for at least one reference lattice subset of the reference orthogonal contingency lattice based on the corresponding subsets in the comparison contingency lattices.

10. The method of claim 9, wherein a significance level of any of the z-scores is adjusted by a Bonferroni correction based on a plurality of comparisons.

11. The method of claim 8, wherein the medical products comprise drugs, medications or vaccines.

12. The method of claim 8, wherein the medical products comprise medical devices.

13. The method of claim 8, further comprising displaying the reference orthogonal contingency lattice with subsets highlighted based on the indication of the interaction between the medical products or conditions.

14. The method of claim 8, wherein the reference orthogonal contingency lattice and the comparison contingency lattices each comprise subsets having a partial order such that between any two subsets there exists a least upper bound subset and a greatest lower bound subset.

15. The method of claim 8, further comprising:
determining, via a processor, a number, N, of patient records in the dataset containing indications of each of the two or more medical products;
of patient records in the dataset containing indications of each of the two or more medical products, determining a number, Nx, of patient records containing indications of the reference condition;
within each of a plurality of random samples of size N of patient records of the dataset, the patient records of the respective random samples containing indications of each of the two or more medical products and combinations thereof but that exclude all the other medical products and combinations thereof, determining a number of such patient records of each random sample containing the reference condition; and
determining whether a second-order bystander effect exists between the reference condition and any of the two or more medical products or combinations thereof based on a comparison of Nx to the number of the patient records of each random sample.

16. The method of claim 15, further comprising graphically displaying the number of patient records containing indications of each of the two or more medical products and combinations thereof but that exclude all the other medical products and combinations thereof of each random sample.

17. A computer implemented method of evaluating interaction of two or more medical products, in the context of a reference condition, based on a dataset of patient records, comprising:

determining a number, N, of patient records in the dataset containing indications of a medical product A and a medical product B;
of patient records in the dataset containing indications of the medical product A and the medical product B, determining a number, Nx, of patient records containing indications of the reference condition;
among patient records of a first random sample of size N of patient records of the dataset, the patient records of the first random sample containing the medical product A and not the medical product B, determining a number of the patient records of the first random sample containing the reference condition;
among patient records of a second random sample of size N of patient records of the dataset, the patient records of the second random sample containing the medical product B and not the medical product A, determining a number of the patient records of the second random sample containing the reference condition;
among patient records of a third random sample of size N of patient records of the dataset, the patient records of the third random sample containing neither the medical product A nor the medical product B, determining a number of the patient records of the third random sample containing the reference condition; and
determining, via a processor, whether a second-order bystander effect exists between the reference condition and either of the medical product A or the medical product B based on a comparison of Nx to the number of the patient records of the first random sample containing the reference condition, the number of the patient records of the second random sample containing the reference condition, and the number of the patient records of the third random sample containing the reference condition.

18. The method of claim 17, wherein the comparison comprises comparing at least 100 of the first random samples, at least 100 of the second random samples and at least 100 of the third random samples.

19. The method of claim 18, further comprising graphically displaying the number of patient records of each of the first random sample, second random sample and third random sample containing indications of the reference condition.

20. The method of claim 17, wherein the two or more medical products comprise drugs, medications or vaccines.

21. The method of claim 17, wherein the two or more medical products comprise medical devices.

22. A computer implemented method of evaluating dependence on demographic variables, in the context of a medical product and a reference condition, based on a dataset of patient records, comprising:
determining a number, N, of patient records in the dataset containing indications of both the medical product and the reference condition;
determining an average demographic variable of the patient records in the dataset containing indications of both the medical product and the reference condition;
for a continuous demographic variable, determining an average of the demographic variable of patient records in a first random sample of size N, the patient records of the first random sample containing an indication of the medical product and not containing an indication of the reference condition;
for the continuous demographic variable, determining an average of the demographic variable of patient records in a second random sample of size N, the patient records of the second random sample containing an indication of the reference condition and not containing an indication of the medical product;

for the continuous demographic variable, determining an average of the demographic variable of patient records in a third random sample of size N, the patient records of the third random sample containing neither an indication of the medical product nor an indication of the reference condition; and determining, via a processor, whether the continuous demographic variable, affects an association between the reference condition and the medical product, wherein the determining step is based on a comparison of the average demographic variable of the patient records in the dataset containing indications of both the medical product and the reference condition, the average of the demographic variable of patient records in a first random sample, the average of the demographic variable of patient records in a second random sample, and the average of the demographic variable of patient records in a third random sample.

23. The method of claim 22, wherein the respective acts of determining an average include determining averages of at least 100 first random samples, at least 100 second random samples and at least 100 third random samples.

24. The method of claim 23, further comprising graphically displaying the averages of the at least 100 first random samples, the averages of the at least 100 second random samples and the averages of the at least 100 third random samples.

25. A computer readable data storage means, the computer readable data storage means not being a transitory signal, and the computer readable data storage means containing program code recorded thereon for implementing the following steps:

developing a reference contingency lattice of reference lattice subsets from a subset of the patient records containing the reference condition, wherein each reference lattice subset corresponds to the patient records that contain the reference condition and that contain a respective medical product or condition, or combination of medical products or conditions, of the two or more medical products or conditions;

developing a plurality of comparison contingency lattices, each of the comparison contingency lattices developed from a respective random subset of the patient records not containing the reference condition, wherein each of the respective random subsets is of a same size as the subset of patient records containing the reference condition, and wherein each of the comparison contingency lattices includes comparison lattice subsets, wherein each comparison lattice subset is associated with a respective reference lattice subset and corresponds to the patient records containing the respective medical product or condition, or combination of medical products or conditions, of the associated reference lattice subset; and comparing, via a processor, the reference lattice subsets of the reference contingency lattice to the associated comparison lattice subsets of the comparison contingency lattices to determine a difference in one of the reference lattice subsets of the reference contingency lattice from the associated comparison lattice subsets of the comparison contingency lattices, wherein the difference is indicative of an interaction between the medical products or conditions with respect to the reference condition.

26. A computing system comprising:

a processor; and a system memory containing program code recorded thereon that when executed by the processor performs the following steps:

developing a reference contingency lattice of reference lattice subsets from a subset of the patient records containing the reference condition, wherein each reference lattice subset corresponds to the patient records that contain the reference condition and that contain a respective medical product or condition, or combination of medical products or conditions, of the two or more medical products or conditions;

developing a plurality of comparison contingency lattices, each of the comparison contingency lattices developed from a respective random subset of the patient records not containing the reference condition, wherein each of the respective random subsets is of a same size as the subset of patient records containing the reference condition, and wherein each of the comparison contingency lattices includes comparison lattice subsets, wherein each comparison lattice subset is associated with a respective reference lattice subset and corresponds to the patient records containing the respective medical product or condition, or combination of medical products or conditions, of the associated reference lattice subset; and comparing, via a processor, the reference lattice subsets of the reference contingency lattice to the associated comparison lattice subsets of the comparison contingency lattices to determine a difference in one of the reference lattice subsets of the reference contingency lattice from the associated comparison lattice subsets of the comparison contingency lattices, wherein the difference is indicative of an interaction between the medical products or conditions with respect to the reference condition.

27. A computer implemented method of evaluating dependence on demographic variables, in the context of a medical product and a reference condition, based on a dataset of patient records, comprising:

determining a number, N, of patient records in the dataset containing indications of both the medical product and the reference condition;

determining a fraction of the patient records in the dataset containing indications of both the medical product and the reference condition;

for a categorical demographic variable, among patient records in a first random sample of size N, determining a fraction of patient records for which the categorical demographic variable has a specified value, the patient records of the first random sample containing an indication of the medical product and not containing an indication of the reference condition;

for the categorical demographic variable, among patient records in a second random sample of size N, determining a fraction of patient records for which the categorical demographic variable has a specified value, the patient records of the second random sample containing an indication of the reference condition and not containing an indication of the medical product;

for the categorical demographic variable, among patient records in a third random sample of size N, determining a fraction of patient records for which the categorical demographic variable has a specified value, the patient records of the third random sample containing neither an indication of the medical product or an indication of the reference condition; and determining, via a processor, whether the categorical demographic variable affects an association between the reference condition and the medical product, wherein the determining step is based on a comparison of the fraction of the patient records in the dataset containing indications of both the medical product and the reference condition, the fraction of patient records for which the categorical demographic variable has the specified value.

28. The method of claim 27, wherein the respective acts of determining a fraction include determining fractions of patient records for which the categorical demographic variable has the specified value in at least 100 fourth random samples, at least 100 fifth random samples and at least 100 sixth random samples.

29. The method of claim 28, further comprising graphically displaying the fractions of patient records for which the categorical demographic variable has the specified value for the at least 100 first random samples, the fractions of patient records for which the categorical demographic variable has the specified value for the at least 100 second random samples and the fractions of patient records for which the categorical demographic variable has the specified value for the at least 100 third random samples.

* * * * *